US009718757B2

(12) United States Patent
Zimmerman et al.

(10) Patent No.: US 9,718,757 B2
(45) Date of Patent: Aug. 1, 2017

(54) SYSTEM AND METHOD FOR SEPARATING LIPID BASED PRODUCTS FROM BIOMASS

(71) Applicant: Yale University, New Haven, CT (US)

(72) Inventors: Julie B. Zimmerman, Guilford, CT (US); Lindsay Soh, Easton, PA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/430,997

(22) PCT Filed: Sep. 27, 2013

(86) PCT No.: PCT/US2013/062289
§ 371 (c)(1),
(2) Date: Mar. 25, 2015

(87) PCT Pub. No.: WO2014/052823
PCT Pub. Date: Apr. 3, 2014

(65) Prior Publication Data
US 2015/0239820 A1    Aug. 27, 2015

Related U.S. Application Data

(60) Provisional application No. 61/706,436, filed on Sep. 27, 2012, provisional application No. 61/794,373, filed on Mar. 15, 2013.

(51) Int. Cl.
| C07C 67/02 | (2006.01) |
| C11B 1/10 | (2006.01) |
| C07C 67/03 | (2006.01) |
| C07C 67/08 | (2006.01) |
| B01J 19/00 | (2006.01) |

(Continued)

(52) U.S. Cl.
CPC ........... *C07C 67/02* (2013.01); *B01J 19/0013* (2013.01); *B01J 19/18* (2013.01); *B01J 19/24* (2013.01); *C07C 67/03* (2013.01); *C07C 67/08* (2013.01); *C07C 67/48* (2013.01); *C10L 1/026* (2013.01); *C11B 1/10* (2013.01); *C11B 1/104* (2013.01); *B01J 2219/00058* (2013.01); *B01J 2219/24* (2013.01); *C10L 2200/0476* (2013.01); *C10L 2270/026* (2013.01); *C10L 2290/543* (2013.01);

(Continued)

(58) Field of Classification Search
None
See application file for complete search history.

(56) References Cited

U.S. PATENT DOCUMENTS 7,122,688 B2 * 10/2006 Lin ................. C07C 67/03
554/169
7,772,414 B1 * 8/2010 Hybertson ............. C10L 1/026
554/12
8,598,378 B2 * 12/2013 Cooney .............. B01D 11/0288
210/638

OTHER PUBLICATIONS

Hekwabu, Z., et al., Solid heterogeneious catalyst for transesterification of triglycerides with methanol: A review, 2009, Applice Catalysis A: General, vol. 363, pp. 1-10.*

(Continued)

*Primary Examiner* — Yate K Cutliff
(74) *Attorney, Agent, or Firm* — Riverside Law LLP

(57) ABSTRACT

Methods and systems for the production and isolation of fatty acid methyl esters (FAMEs) from a lipid source are described. The method includes extracting a lipid from a lipid source and transesterifying the lipid into a FAME. The method may also include fractionating the FAME from the system. A method of selectively transesterifying a lipid into a FAME is also described.

39 Claims, 18 Drawing Sheets

(51) Int. Cl.
  B01J 19/18    (2006.01)
  B01J 19/24    (2006.01)
  C07C 67/48    (2006.01)
  C10L 1/02     (2006.01)
  C11C 3/00     (2006.01)
(52) U.S. Cl.
  CPC ......... C10L 2290/544 (2013.01); C11C 3/003 (2013.01); Y02E 50/13 (2013.01)

(56) References Cited

OTHER PUBLICATIONS

Ferrentino, J., Microalgal oil extraction and in situ transesterification, 2007, dissertation presented to the University of New Hampshire, pub. No. MT 1447885, 108 pages.*

Soh et al., "One-Pot Algal Biodiesel Production in Supercritical Carbon Dioxide," 2012, International Society for Supercritical Fluid, San Francisco, CA, May 13-16, 8 pages.

Soh et al., 2011, "Biodiesel production: the potential of algal lipids extracted with supercritical carbon dioxide," Green Chem. 13:1422-1429.

Patil et al., 2011, "Optimization of direct conversion of wet algae to biodiesel under supercritical methanol conditions," Bioresource Tech. 102:118-122.

Kiwjaroun et al., 2009, "LCA studies comparing biodiesel synthesized by conventional and supercritical methanol methods," J. Cleaner Prod. 17:143-153.

Bertoldi et al., 2009, "Continuous Production of Biodiesel from Soybean Oil in Supercritical Ethanol and Carbon Dioxide as Cosolvent," Energy & Fuels 23:5165-5172.

Han et al., 2005, "Preparation of biodiesel from soybean oil using supercritical methanol and CO2 as co-solvent," Proc. Biochem. 40:3148-3151.

Maçaira et al., 2011, "Biodiesel production using supercritical methanol/carbon dioxide mixtures in a continuous reactor," Fuel 90:2280-2288.

Jackson and King, 1996, "Methanolysis of seed oils in flowing supercritical carbon dioxide," J. Amer. Oil Chem. Soc. 73:353-356.

Galia et al., 2011, "Transesterification of rapeseed oil over acid resins promoted by supercritical carbon dioxide," J. Supercrit. Fluid 56:186-193.

Oliveira et al., 2009, "Phase equilibria of glycerol containing systems and their description with the Cubic-Plus-Association (CPA) Equation of State," Fluid Phase Equilib. 280:22-29.

Bharath et al., 1989, "Vapor-liquid equilibria for binary mixtures of carbon dioxide and fatty acid ethyl esters," Fluid Phase Equilib. 50:315-327.

Inomata et al., 1989, "Vapour—liquid equilibria for binary mixtures of carbon dioxide and fatty acid methyl esters," Fluid Phase Equilib. 46:41-52.

* cited by examiner

| Extracted or finished components | | Value (US/ton 5/25/12 data points) | Percent by weight Crude oil | Percent by weight Refined (i.e., corn oil, palm oil) |
|---|---|---|---|---|
| Lipid | TAG C14:0 | 3,700-3,830[a] | - | 6.5[e] |
| | C16:0 | 1,050-1,110[a] | 11[d] | 36.1[e] |
| | C18:0 | 1,040-1,130[a] | 4[d] | 1.1[e] |
| | C18:1 | 1,450-1,580[a] | 24[d] | 19.7[e] |
| | C18:2 | 31,000-54,000[a] | 54[d] | 1.2[e] |
| | C18:3 | 10,000-34,000[a] | 7[d] | - |
| | other fatty acids | | 16[d] | 35.4 (C16:1 = 27.6)[e] |
| | Omega-3 fatty acid | 1,000-12,000,000[b] | 20[d] | 16[f] |
| | | | | 6.8[e] |
| | Sterols | 16,000-20,000[b] | >1.5[d] | >1[e] |
| | Pigments (i.e., beta carotene) | 100-30,000[c] | >2[d] | >3[e] |
| | phospholipids | 1000-1,000,000[b] | 2[d] | 2[e] |
| Carbohydrate | | | 35[d] | 16[e] |
| Protein | | 300-600[b] | 40[d] | 60[e] |
| Biodiesel | | 800[b] | | |
| Glycerin | | 400[b] | | |

Figure 1

SYSTEM AND METHOD FOR SEPARATING LIPID BASED PRODUCTS FROM BIOMASS

CROSS-REFERENCE TO RELATED APPLICATIONS

This application is the U.S. national stage application filed under 35 U.S.C. §371 claiming benefit to International Patent Application No. PCT/US13/62289, filed Sep. 27, 2013, which is entitled to priority under 35 U.S.C. §119(e) to U.S. Provisional Applications No. 61/706,436, filed Sep. 27, 2012, and No. 61/794,373, filed Mar. 15, 2013, all of which applications are hereby incorporated by reference in their entireties herein.

STATEMENT REGARDING FEDERALLY SPONSORED RESEARCH OR DEVELOPMENT

This invention was made with government support under FP-91717301-0 awarded by the Environmental Protection Agency (EPA). The government has certain rights in the invention.

BACKGROUND OF THE INVENTION

There is an increasing demand to produce transportation fuels from renewable resources as evidenced through the Energy Independence and Security Act of 2007 (Bingaman, 2007, from the Energy Independence and Security Act of 2007). Biodiesel offers a sustainable alternative to traditional fossil based fuels as it is sourced from a renewable feedstock, with other advantages in that it is cleaner burning than diesel, safer to handle, and promotes longer engine life (Bozbas, 2008, Renew. Sustain. Energy Rev. 12, 542-552). Additionally, biodiesel provides a direct drop-in replacement for petroleum-based diesel fuel and can be used in other applications, for example, boilers (Carraretto et al., 2004, Energy 29:2195-2211). While biofuels (both biodiesel and bioethanol) provide a potentially sustainable fuel source, significant gains towards a favorable energy balance for fuel production would arise from lowering the agricultural inputs required for feedstock production (fertilizers, pesticides, etc.), producing crops on less desirable land, lowering the energy involved with extraction of desirable components and conversion into the fuel, as well as developing a reliable stream of value-added co-products (Hill et al., 2006, Proc. Natl. Acad. Sci. 103:11206-11210).

Life cycle analyses (LCA) of the biodiesel production process from various renewable feedstocks (Yee et al., 2009, App. Energy 86:S189-S196; Bernesson et al., 2004, Biomass and Bioenergy 26:545-559; Brenter et al., 2011, Environ. Sci. Tech. 45:7060-7067; Janulis, 2004, Renew. Energy 29:861-871; Lardon et al., 2009, 43:6475-6481; Gerpen, 2005, Fuel Process. Tech. 86:1097-1107; Kiwjaroun et al., 2009, J. Cleaner Prod. 17:143-153) show that significant energy requirements are involved with the growth of the fuel feedstock as well as lipid extraction and conversion. Several of these LCAs have specifically compared different means for lipid extraction and conversion (Brenter et al., 2011, Environ. Sci. Tech. 45:7060-7067; Lardon et al., 2009, 43:6475-6481; Kiwjaroun et al., 2009, J. Cleaner Prod. 17:143-153). From these studies it can be concluded that compared to current technologies for transesterification, significant benefits can be achieved from more selective and energy efficient processes. One of these studies analyzed biodiesel production from algae and suggested that one-step extraction of triacylglycerides and conversion via transesterification using supercritical methanol (scMeOH) (Patil et al., 2011, Bioresource Tech. 102:118-122) has the greatest potential in terms of minimizing energy requirements.

These gains could be realized since the process does not require dried algae as a starting material, and it combines the two processing steps (extraction and conversion) into a single step, which would minimize the energy needed for solvent production and product separations. While this technology offers energy savings over the base case there is still a question of a positive energy balance mainly due to the high heating requirements associated with producing supercritical methanol.

Another study assessing the transesterification of palm oil analyzed in detail the use of scMeOH for the transesterification of triacylglycerides (Kiwjaroun et al., 2009, J. Cleaner Prod. 17:143-153). This study indicated that while the use of scMeOH provides benefits in terms of improvements to fuel quality, that significant advances must be made in order to decrease the significantly elevated energy needs of producing scMeOH. These high energy requirements may be mediated by lowering the reaction temperature and pressure, as well as by lowering the energy associated with methanol recovery. A critical step towards a more efficient pathway for biodiesel production would be to address the high energy demands of scMeOH transesterification associated with the high critical temperature.

Supercritical transesterification of triacylglyceride feedstocks has been demonstrated using both methanol and ethanol (Pinnarat and Savge, 2008, Ind. Engineer. Chem. Res. 47:6801-6808; Sawangkeaw et al., 2010, J. Supercrit. Fluids 55:1-13). Generally it was found that the most desirable reaction conditions for non-catalytic supercritical transesterification of triacylglyceride feedstocks is between 250-400° C., 19-45 MPa, with approximately a 40:1 methanol to TAG molar ratio for a period of time between 4 and 30 minutes. The use of neat methanol would appear to be the more efficient route, yet it has been determined that methanol and typical triacylglycerides do not form a single phase at temperatures below 225° C. (Hegel et al., 2008, Fluid Phase Equil. 266:31-37; Tang et al., 2006, Fluid Phase Equil. 239:8-11; CerCe et al., 2005, Ind. Engineer Chem. Res. 44:9535-9541). As such, equipment costs and energy demand are significantly elevated for neat methanol systems that must operate in a single fluid phase for reasonable yields. The use of catalysts and/or co-solvents has been explored to moderate these reaction conditions (Cao et al., 2005, Fuel 84:347-351; Demirbas, 2008, Energy Sources, Part A: Recovery, Utilization, and Environmental Effects, 30:1830-1834; Patil et al., 2009, Energy & Fuels 24:746-751). Co-solvents such as propane or hexane (Cao et al., 2005, Fuel 84:347-351) have been added to supercritical methanol in order to form a single fluid phase at less energy intensive conditions. While this strategy is successful from a phase behavior perspective (at mild pressures), it is burdened by flammability issues. Additionally, both the use of neat methanol and methanol/organic co-solvent gives rise to an additional problem in downstream separations of the reaction products. Both fatty acid methyl esters (FAME) and glycerol products are soluble in methanol (Hegel et al., 2008, Fluid Phase Equil. 266:31-37) incurring potentially high separation costs in order to recover the desirable product, FAME, and isolate the undesirable by-product, glycerol. The use of homogeneous catalysts in supercritical transesterification (Patil et al., 2009, Energy & Fuels 24:746-751) may also mediate reaction conditions but has similar challenges in terms downstream separation issues.

Carbon dioxide ($CO_2$) has been used as a co-solvent for transesterification in both supercritical ethanol (Bertoldi et al., 2009, Energy & Fuels 23:5165-*5172 and methanol (Han et al., 2005, Proc. Biochem. 40:3148-3151) with the aim of reducing reaction temperatures and pressures. It was found to be effective at percentages up to 10% $CO_2$, but temperatures still needed to be at least 280° C. in order for the reaction to reach a 98% yield (Han et al., 2005, Proc. Biochem. 40:3148-3151). Two studies explored using methanol in continuous reactors with supercritical $CO_2$ (sc$CO_2$) over fixed catalyst beds (Maçaira et al., 2011, Fuel 90:2280-2288; Jackson and King, 1996, J. Amer. Oil Chem. Soc. 73:353-356). The first flowed sc$CO_2$ over a bed of lipase finding 98% yield of FAME (Jackson and King, 1996, J. Amer. Oil Chem. Soc. 73:353-356), but high pressures of 17.2 MPa and the expensive catalyst pose potential challenges for scale up and commercialization. The other study used a packed bed of Nafion®-SAC13 in a continuous system consisting of 75:25 $CO_2$:methanol. This study also required high temperatures and pressures (200° C., 25 MPa) (Macaira et al., 2011, Fuel 90:2280-2288). In addition to high pressures, both studies suffered from difficulties pertaining to the downstream separation of glycerol from the product. The use of $CO_2$ in these systems facilitates the solubility of the triacylglyceride and methanol, but the requirement of supercritical conditions may not be necessary in order to benefit from using $CO_2$ (i.e. increased solubility and selectivity as well as decreased mass transfer resistance).

Operating at lower temperatures and pressures in a multiphase, liquid-vapor system, may allow for similar benefits without such high energy burdens (Beckman, 2003, Environ. Sci. Tech. 37:5289-5296). One other study has assessed the transesterification of rapeseed oil with sc$CO_2$ and methanol over sulfonated polymer matrices (Galia et al., 2011, J. Supercrit. Fluid 56:186-193). The authors achieved a maximal 62.4% yield at 140° C. and 11.0 MPa during an 8 h reaction (Methanol/oil 27.7 mol/mol, catalyst loading of 10% w/w substrate). This work undertakes a more fundamental approach to comprehend this complex system consisting of $CO_2$, methanol, substrate, and catalyst and inform the experimental conditions favourable for reaction. Understanding the fluid phase behavior that will contribute to high reaction yields while minimizing the required process energy will be key to efficient transesterification. $CO_2$ has great potential for efficient extraction and production of various fuel and non-fuel products due to its selectivity and flexibility. Efficient process design could not only allow for great energy savings but also support the concept of a biorefinery (Foley et al., 2011, Green Chem. 13:1399-1405) where fuel as well as value-added chemicals can be efficiently produced to increase economic favorability of renewable feedstocks.

Full utilization of biomass for fuels and valuable co-products, analogous to petroleum refining for a wide spectrum of products, has been put forward as a critical research goal. For example, the US DOE Energy Efficiency & Renewable Energy Integrated Biorefinery Program highlights the importance of co-products from energy crops, agricultural residues, and microalgae, to reduce economic and environmental barriers to large-scale fuel production (DOE/EE-0767: Integrated Biorefineries: Biofuels, Biopower, and Bioproducts: www1.eere.energy.gov/biomass/pdfs/ibr_portfolio_overview.pdf). Currently, many of the co-products are diverted to low-value uses such as animal feed, anaerobic digestion, and nutrient recycling via fertilizers. However, in many biomass supplies the lipid components represent a higher-value, non-fuel product palette including nutritional supplements, feedstocks for bioplastics, and surfactants (IEA Bioenergy, "Bio-based Chemicals: Value-Added Products from Biorefineries", 2012). The molecular components of the lipid fraction are typically triacylglycerides (TAGs), a non-polar fraction used as the precursor to biodiesel but also phospholipids, pigments, anti-oxidants, and sterols. Recent market data shows order-of-magnitude differences in the value of the various fatty acid fractions from TAG, the non-TAG lipids, and fuel or co-products (ICIS Pricing: 8 Aug. 2012, Fatty Acids—Fractionated (Asia Pacific): www.icispricing.com/il_shared/Samples/SubPage227.asp). In particular, the chain length and degree of unsaturation of individual fatty acids in TAGs strongly affects their value. In order to ensure the viability and sustainability of bio-based fuels, it is imperative to effectively take advantage of these differences in value in an integrated biorefinery.

Total biomass production via photosynthesis is estimated to be 200 billion tons/year, with less than 0.1% used by humans for non-nutritive purposes (Zoebelein, H., 2001, Dictionary of Renewable Resources. 2nd ed.; Wiley-VCH: Weinheim, Germany). Non-animal oils are found in highest concentrations in seeds (soybean, cotton), fruit pulps (palm, coconut), and various microalgae. The oil content varies widely and is rarely the major component of the raw biomass, which also contains protein and carbohydrate (Griffiths et al., 2011, J. Appl. Phycol. 24:989-1001; Liu, 1997, Soybeans: Chemistry, Technology, and Utilization. Chapman & Hall: New York). Depending on species and growth conditions, the oil fraction may contain a wide variety of nonpolar and polar lipids ranging from triacylglycerides, free fatty acids, phospholipids, antioxidants, pigments, vitamins, and sterols. Chain length and degree of unsaturation of the fatty acids and their derivatives are also highly variable. Separation and processing techniques that are robust and can tolerate varying biomass compositions will enable biorefineries to adapt to and efficiently use broader ranges of raw materials, and optimize for economic and environmental benefits.

The conventional approach to lipid extraction, processing, and refining involves pretreatment steps (pressing, wet or dry rendering), solvent extraction (e.g. hexane, chloroform/methanol), and often centrifuging to remove residue from water and oil phases. These methods are non-selective, yielding TAG as well as other lipid components including pigments, sterols, and phospholipids. Phospholipids may be separated by steam or chemical treatment, and free fatty acids removed by distillation or alkaline water washes (Zoebelein, H., 2001, Dictionary of Renewable Resources. 2nd ed.; Wiley-VCH: Weinheim, Germany). Further processing of TAG to isolate desired fractions is common. For example, processing of coconut fatty acids for use in surfactants requires additional energy-intensive steps: TAGs are hydrolyzed at high temperature and moderate pressure (250° C., 5 MPa) followed by vacuum distillation at 200° C. (Gervajio, 2012, Fatty Acids and Derivatives from Coconut Oil. In Kirk-Othmer Encyclopedia of Chemical Technology, Wiley). In the case of polyunsaturated fatty acids (PUFAs), which are sensitive to high temperatures, the isolated total lipids are typically converted to urea inclusion compounds and then undergo cryogenic fractional distillation at −20 to −70° C. (Mishra et al., 1993, Food Res. Int. 26:217-226) or chromatographic techniques involving $AgNO_3$-modified solid phases, which are difficult to employ on a larger scale (Chester et al., 1996, Anal. Chem. 68:487R-514R).

In the production of biodiesel, extraction of lipids from biomass is followed by a stepwise transesterification reaction producing three fatty acid methyl ester (FAME) molecules for every molecule of TAG. Diglycerides (DGs) and monoglycerides (MGs) are produced as intermediates, with glycerol as a by-product of the overall reaction. The first step of the reaction (TAG to DG) is generally considered the rate-limiting step under ambient conditions, but the impact of solvent density has yet to be definitively determined (Lopez et al., 2007, J. Catal. 245:381-391). Since complete transesterification of one TAG molecule requires 3 molecules of alcohol, a minimal 3:1 molar ratio of methanol (or other alcohol) to substrate is required. To move from a second order to a pseudo-first order kinetics, excess methanol ratios are generally used (Fukuda et al., 2001, J. Biosci. Bioeng. 92:405-416). However, there is the potential for diminishing returns with excessive methanol ratios since high concentrations of methanol can adversely impact phase behavior in a mixed $CO_2$ system (i.e., decreasing the solubility of TAG in the system).

In addition to an alcohol, the transesterification step typically requires an acidic, basic or enzymatic catalyst to carry out the reaction at temperatures below 100° C. Acidic catalysts can be used in feedstocks that may be contaminated with free fatty acids or water, preventing saponification that would occur with basic catalysts. However, basic catalysts have faster reaction kinetics than acidic catalysts (Fukuda et al., 2001, J. Biosci. Bioeng. 92:405-416). Lipases are also used for transesterification requiring a lower operating temperature, but are expensive compared to the alternatives (Fukuda et al., 2001, J. Biosci. Bioeng. 92:405-416), and reported yields under supercritical conditions are relatively low (Madras et al., 2004, Fuel 83:2029-2033; Taher et al., 2011, Biochem. Eng. J. 55:23-31).

There is a need in the art for energy-efficient methods of isolating biodiesel and other lipid-based products from biomass. The present invention addresses this unmet need.

BRIEF SUMMARY OF THE INVENTION

The present invention includes a method for producing a fatty acid methyl ester (FAME) from a lipid source. The method comprises extracting at least one lipid from a lipid source; and transesterifying the at least one lipid into a FAME, wherein the steps of extracting and transesterifying occur within a system comprised of a first solvent and a second solvent, and at least one catalyst.

In one embodiment, the method further comprises the step of fractionating the FAME from the system. In another embodiment, the at least one lipid is a triacylglyceride (TAG). In yet another embodiment, the lipid source comprises biomass. In yet another embodiment, the biomass comprises algae. In yet another embodiment, the biomass is dry biomass. In yet another embodiment, the biomass is wet biomass. In yet another embodiment, the first solvent is a polar solvent. In yet another embodiment, the polar solvent is methanol. In yet another embodiment, the first solvent is present within the system at a volume of about 3.6% v/v. In yet another embodiment, the second solvent is a supercritical fluid. In yet another embodiment, the supercritical fluid is supercritical carbon dioxide. In yet another embodiment, the catalyst is a heterogenous catalyst. In yet another embodiment, the heterogenous catalyst is Nafion®. In yet another embodiment, the system is heated to a temperature no greater than about 95° C. In yet another embodiment, the system is heated to a temperature no greater than about 80° C. In yet another embodiment, the system is pressurized to a pressure of about 9.5 MPa. In yet another embodiment, the system is pressurized to a pressure of about 9.65 MPa. In yet another embodiment, the system is pressurized to a pressure of about 17.5 MPa. In yet another embodiment, the system has a reaction time of at least 2 hours.

The present invention also includes a method for selectively producing a fatty acid methyl ester (FAME) from a lipid source. The method comprises extracting at least one lipid from a lipid source, selectively transesterifying the at least one lipid into a FAME, and fractionating the FAME, wherein the lipid source is comprised of a mixture of lipids, further wherein the steps of extracting and transesterifying occur within a system, further wherein the system is comprised of a first solvent and a second solvent, and further wherein the system is comprised of a catalyst.

In one embodiment, the at least one lipid is a triacylglyceride (TAG). In another embodiment, the lipid source comprises biomass. In yet another embodiment, the biomass comprises algae. In yet another embodiment, the biomass is dry biomass. In yet another embodiment, the biomass is wet biomass. In yet another embodiment, the first solvent is a polar solvent. In yet another embodiment, the polar solvent is methanol. In yet another embodiment, the first solvent is present within the system at a volume of about 3.6% v/v. In yet another embodiment, the second solvent is a supercritical fluid. In yet another embodiment, the supercritical fluid is supercritical carbon dioxide. In yet another embodiment, the catalyst is a heterogenous catalyst. In yet another embodiment, the heterogenous catalyst is Nafion®. In yet another embodiment, the system is heated to a temperature no greater than about 95° C. In yet another embodiment, the system is heated to a temperature no greater than about 80° C. In yet another embodiment, the system is pressurized to a pressure of about 9.5 MPa. In yet another embodiment, the system is pressurized to a pressure of about 9.65 MPa. In yet another embodiment, the system is pressurized to a pressure of about 17.5 MPa. In yet another embodiment, the system has a reaction time of at least 2 hours.

The present invention also includes a system for producing a fatty acid methyl ester (FAME) from a lipid source. The system comprises a reaction vessel for extracting at least one lipid from the lipid source and for transesterifying the at least one lipid into the FAME and having at least one inlet passage and at least one outlet passage, wherein a reaction component enters the reaction vessel through the inlet passage and exits the reaction vessel through the outlet passage.

In one embodiment, the reaction vessel is a reactor. In another embodiment, the FAME is fractionated from the reaction vessel. In yet another embodiment, the reaction vessel has a fixed volume. In yet another embodiment, the system further comprises a thermocouple to adjust the temperature of the system. In yet another embodiment, the system further comprises a stirring mechanism for stirring the reaction components within the reaction vessel. In yet another embodiment, the system further comprises a collection vessel for the collection of the FAME which has exited the reaction vessel.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 is a table illustrating a comparison between soy and algae biomass and the economic value of component fractions.

FIGS. 4A-4B, illustrates cloud point curves of various solvents. FIG. 4A is a graph illustrating cloud point curves of glycerol plus various loadings of methanol. The inset highlights the low weight percent region. FIG. 4B is a graph illustrating cloud point curves of triolein plus various loadings of methanol. Methanol was loaded at 40° C. S=substrate (FIG. 4A, S=glycerol; FIG. 4B: S=triolein).

FIG. 7A is a graph illustrating experimental conditions for transesterification using triolein as a substrate. FIG. 7B is a graph illustrating experimental conditions for transesterification using diolein as a substrate. FIG. 7C is a graph illustrating experimental conditions for transesterification using monoolein as a substrate. Reactions were carried out under varying methanol loadings (0.6 or 2.5 mL in 50 mL vessel), temperature (40° C. or 60° C.), and pressure (9.5 MPa or 17.5 MPa). All experiments used 10 mg of substrate, 500 mg of Nafion® with a reaction time for 2 h. Pictured values were the average of at least duplicate samples.

FIGS. 8A-8B, illustrates cloud points and bubble points. FIG. 8A is a graph illustrating cloud points and bubble points for triolein. FIG. 8B is a graph illustrating cloud points and bubble points for diolein. Data was collected at 80° C. with methanol to substrate ratios replicating experimental conditions. Points correlating with substrate compositions described in Table 1: Entry 4 (●; Entry 8 (●). Solid phase from catalyst is not included in the data. Figure legend: Cloud points (■); bubble points (▲).

FIG. 11A is a schematic illustrating an overview of the biorefinery concept based on mass of products. FIG. 11B is a schematic illustrating an overview of the biorefinery concept based on the economic value of products. The thickness of each arrow indicates the percentage of mass (FIG. 11A) and economic value (FIG. 11B) associated with each fraction of products (referred to in Table 1).

FIGS. 14A-14B, illustrates the percent yields of FAME and unconverted triacylglycerides. FIG. 14A is a graph illustrating the results of five individual experiments in which a single, pure triacylglyceride was converted to the corresponding fatty acid methyl ester. FIG. 14B is a graph illustrating the results of a single experiment where the substrate consists of equal portions of the same five triacylglycerides. Reaction conditions: 95° C., 9.65 MPa, 3.6% methanol (v/v$_{reactor}$, ambient), 1 h reaction, 100 mg total substrate, 0.36 mmol Nafion® NR50.

FIG. 18A is a graph of transesterification using hydrotalcite as catalyst. FIG. 18B is a graph of transesterification using zeolite as catalyst. FIG. 18C is a graph of transesterification using Nafion® as catalyst.

FIG. 18D is a graph of transesterification using mesoporous silica as catalyst. Reactions were conducted ambient pressure in methanol at 100° C.

DETAILED DESCRIPTION

Figure 2:
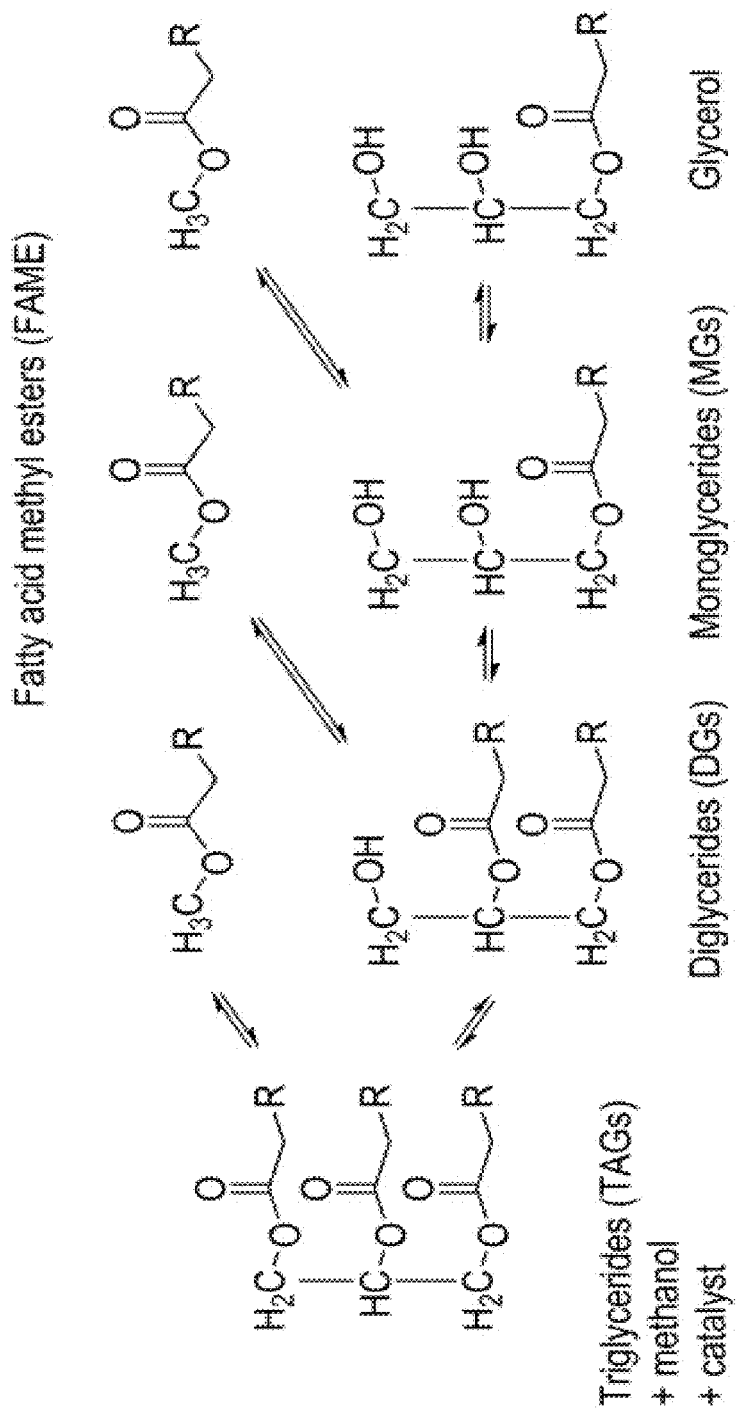
FIG. 2 is a schematic illustrating the transesterification of triacylglycerides (TAG) to fatty acid methyl esters (FAME), where methanol is used for the transesterification reaction.
Figure 3:
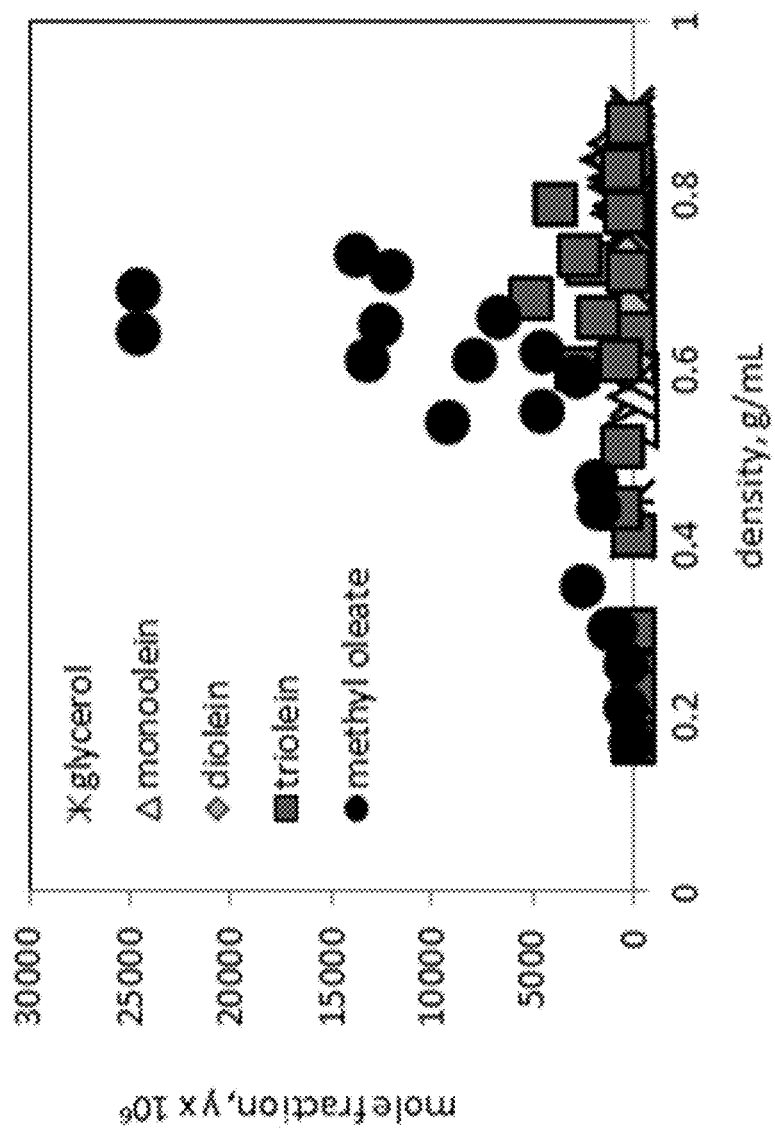
FIG. 3 is a graph illustrating the solubilities of different oleate substrates in $scCO_2$.

The present invention relates to the discovery that triacylglycerides (TAGs) can be extracted from biomass and subsequently converted into fatty acid methyl esters (FAMEs) using a method which combines both steps within one system. Thus, the present invention provides systems and methods for the production and isolation of FAME and other lipid products from a lipid source. In some embodiments, the lipid source is biomass. This system is comprised of at least two different solvents and at least one heterogenous catalyst. In some embodiments, the at least two different solvents are supercritical $CO_2$ ($scCO_2$) and methanol. In some embodiments, the at least one heterogenous catalyst is a perflourosulfonic acid resin catalyst, such as Nafion®.

The present invention also relates to the discovery that certain TAGs may be selectively converted into FAMEs in the presence of other TAGs. The FAMEs can subsequently be separated from the unreacted TAGs in a fractionation step. In some embodiments, the systems and methods of the present invention further comprise a fractionation step.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "lipid" as used herein means a substance that is soluble in organic solvents and includes, but is not limited to, oils, fats, triacylglycerides, fatty acids and phospholipids.

An "alkyl" group is a saturated hydrocarbyl group having from one to twenty carbon atoms in a linear, branched or cyclic arrangement. In one preferred embodiment, alkyl groups are acyclic.

The term "critical point," as used herein, refers to the point at which the liquid and vapour state of a substance become identical. A substance can be, for example, a fluid or a gas. Above but close to the critical point of a substance, the substance is in a fluid state that has properties of both liquids and gases. The fluid has a density similar to a liquid, and viscosity and diffusivity similar to a gas. The term "supercritical" as used herein refers to the pressure-temperature region above the critical point of a substance. The term "subcritical" as used herein refers to the pressure-temperature region equal to or above the vapour pressure for the liquid, but below the critical temperature. The term "near critical" as used herein encompasses both "supercritical" and "subcritical" regions, and refers to pressures and temperatures near the critical point. The terms "fractionate," "fractionating," "fractioned" or "fractionation," as used herein, mean the selective removal of a lipid from the system over other lipids present within the same system. In some instances, the selective removal of the lipid may be due to the difference in solubility of the lipid as compared to the other lipids or to the affinity and/or reactivity of the lipid toward the catalyst as compared to the other lipids. Thus, the term "fractionating" or its related forms can mean removing the lipid from the system to form a mixture comprising isolated lipids, or it can be used to mean physically isolating and separating the desired lipid from the system.

The term "ambient conditions," as used herein, refers to surrounding conditions at about one atmosphere of pressure and about 25° C.

The term "Nafion®" refers to a perflourosulfonic acid resin catalyst.

The term "biodiesel" as used herein refers to methyl, ethyl, or any alkyl esters of fatty acids derived from biomass.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the discovery that triacylglycerides (TAGs) can be extracted from biomass and subsequently converted into fatty acid methyl esters (FAMEs) using a method which combines both steps within one system. Thus, the present invention provides systems and methods for the production and isolation of FAMEs and other lipid products from a lipid source. In some embodiments, the lipid source is biomass. This system is comprised of at least two different solvents and at least one heterogenous catalyst. In some embodiments, the at least two different solvents are supercritical $CO_2$ ($scCO_2$) and methanol. In some embodiments, the at least one heterogenous catalyst is a perflourosulfonic acid resin catalyst, such as Nafion®.

The present invention also relates to the discovery that certain TAGs may be selectively transesterified into FAMEs in the presence of other TAGs. The FAMEs can subsequently be separated from the unreacted TAGs in a fractionation step. In some embodiments, the systems and methods of the present invention further comprise a fractionation step.

Biomass contains a wide variety of lipids, such as TAGs, which are useful as fuels and other chemical products. The TAGs can be extracted from the biomass and subsequently converted into a number of products, such as diglycerides (DGs), monoglycerides (MGs), glycerol, and FAMEs, through a transesterification reaction with an alcohol. Of the products resulting from the transesterification reaction, FAMEs are particularly desirable because they can be used in a number of lipid-based products, such as biodiesel (FIG. 1). Thus, the present invention provides systems and methods related to the production and isolation of FAMEs from biomass.

In the systems and methods of the present invention, both processes for the production of a FAME from a lipid source (i.e. the extraction of a TAG from the lipid source and the conversion of the TAG to the FAME via a transesterification reaction) are performed within a single system. The present invention provides advantages over the prior art because when using the methods and systems of the present invention, FAME can be produced at near-quantitative yields under considerably milder conditions than current processes and through the elimination of downstream processing and separation steps. Furthermore, the present invention provides systems and methods for this selective transesterification process, which permits the isolation of specific lipid fractions from the lipid source for fuel and other products requiring a particular set of lipids such as nutritional supplements, feedstocks for bioplastics, and surfactants.

Lipid Sources

The present invention relates to the production and isolation of a FAME and/or another co-product from a lipid source. A lipid source of the present invention comprises at least one lipid. Any lipid that can undergo a transesterification reaction is contemplated for use within the systems and methods of the present invention, as would be understood by one skilled in the art. Non limiting examples of lipids include TAGs, diglycerides (DGs), and monoglycerides (MGs). In certain embodiments, the lipid is a triacylglyceride. Examples of triacylglycerides include, but are not limited to, tripalmitin, tristearin, triolein, trilinolein, and trilinolenin. In some embodiments, the lipid source is an oil. The oil may be from any source, such as from plant or fruit seeds or from animal fat. In one embodiment, the oil is canola oil. In another embodiment, the oil is palm oil. In another embodiment, the oil is coconut oil.

In certain embodiments, the lipid source is biomass. As used herein, the term "biomass" refers to any organic source of energy or chemicals that is renewable. The biomass may be from any source. Biomass may be derived from a single source, or biomass can comprise a mixture derived from more than one source; for example, biomass could comprise a mixture of algae and seaweed, or a mixture of grass and legumes. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, algae and other marine plants, non-animal oils, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits and fruit pulps, flowers, and animal manure or a combination thereof.

In certain embodiments, the biomass is comprised of algae. As contemplated herein, any species of algae may be used within the systems and methods of the present invention. In some embodiments, the algae is a microalgae. In some embodiments, the microalgae is a member of the class Prymnesiophyceae. In some embodiments, the microalgae is a member of the genus *Isochrysis*. In one embodiment, the microalgae is *Isochrysis galbana*. In some embodiments, the microalgae is a member of the class Chlorophyceae. In some embodiments, the microalgae is a member of the genus *Scenedesmus*. In one embodiment, the microalgae is *Scenedesmus dimorphus*.

In some embodiments, the biomass is dried or dewatered prior to being processed by the systems and methods of the present invention. The term "dewatered" as used herein refers to the removal of at least some water. Methods of drying or dewatering biomass are known in the art. Non-limiting methods of drying biomass include ambient air drying, forced air drying, kiln drying, torrefaction, and lyophylization. Non-limiting methods of dewatering biomass include filtration, centrifugation, heating, flocculation, sedimentation or flotation.

In preferred embodiments, the biomass is wet when processed by the systems and methods of the present invention. Wet biomass is preferred for use in the present invention because the need for a drying or dewatering step and/or upstream or downstream water removal steps is eliminated, thereby reducing the energy requirements of the overall process and thus minimizing its impact on the environment.

Extraction and Transesterification

The present invention provides systems and methods for the production and isolation of a FAME from a lipid source. The production of a FAME from a lipid source may be performed in two steps, where the first step comprises extraction of at least one lipid from a lipid source and the second step comprises the transesterification of the lipid into a FAME. Although each of these steps may be performed separately from each other, it is more energetically favorable to perform both steps simultaneously within the same system. As such, the systems and methods of producing a FAME from a lipid source described herein are comprised of both the step of extracting at least one lipid from the lipid source and the step of transesterifying the lipid into the FAME. The systems of the present invention are comprised of a number of variables that can be adjusted in order to effectively transesterify the lipid or lipids. These variables include solvents, volume of solvent, temperature, pressure, catalyst, and reaction time.

In certain embodiments of the present invention, the system is comprised of a first solvent and a second solvent. In certain embodiments, the first solvent is a polar solvent. Non-limiting examples of polar solvents include methanol, ethanol, isopropanol, acetone, ethyl acetate, and acetonitrile. The first solvent is preferably an alcohol because an alcohol can serve a dual role as both a solvent and reactant during the transesterification reaction. In some embodiments, the second solvent is a non-polar solvent. Non-limiting examples of non-polar solvents include hexane, hexene, octane, pentane, cyclohexane, iso-octane, and 1-hexene. In some embodiments, the second solvent is a subcritical fluid. In one embodiment, the second solvent is subcritical $CO_2$. In certain embodiments, the second solvent is a supercritical fluid. Non-limiting examples of supercritical fluids include supercritical carbon dioxide ($scCO_2$) and supercritical methanol (scMeOH). In one embodiment, the first solvent is methanol and the second solvent is $scCO_2$. Methanol is a polar solvent, and $scCO_2$ exhibits non-polar behavior. Because both the extraction and transesterification steps are occurring within the same system as described elsewhere herein, the system is comprised of an ever-changing composition of substrates. For example, the conversion of TAGs to FAMEs includes a number of substrates including TAGs, diglycerides (DGs), monoglycerides (MGs), glycerol, and FAMEs (FIG. 2). The polarity of these particular substrates ranges from the least polar (TAGs) to the most polar (glycerol). The combination of a polar solvent and a non-polar solvent in the system provides an environment where polar and non-polar substrates achieve varying degrees of solubility, which is thermodynamically favorable for driving the transesterification reaction in the forward direction toward product formation. In some embodiments, the first solvent, the second solvent, and the substrate form a single phase within the system. In other embodiments, the first solvent, the second solvent, and the substrate form two or more phases within the system. When two or more phases are formed within the system, the products of the reaction may preferably partition into the polar solvent rather than the non-polar solvent, or vice versa, depending upon their polarities, thereby facilitating product isolation. In other embodiments, the system is further comprised of at least one additional solvent. In one embodiment, the at least one additional solvent is ethyl acetate.

The volume of the first solvent of the system can be any volume that is capable of solubilizing at least a portion of the lipid and/or any additional substrates in order to drive the transesterification reaction in the forward direction toward product formation. In one embodiment, the volume of the first solvent is between 0.1% v/v and 99.9% v/v. As used herein, the term "v/v" refers to the (volume of the first solvent/total volume of the system at ambient conditions)× 100%. In another embodiment, the volume of the first solvent is between 0.5% v/v and 50% v/v. In yet another embodiment, the volume of the first solvent is between 1% v/v and 25% v/v. In yet another embodiment, the volume of the first solvent is between 2% v/v and 10% v/v. In yet another embodiment, the volume of the first solvent is between 3% v/v and 5% v/v. In a certain embodiment, the volume of methanol is 3.6% v/v. In another embodiment, the volume of methanol is 10% v/v.

In some embodiments, the system is heated in a temperature range from 30° C. to 200° C. In one embodiment, the temperature is no greater than 200° C. In one embodiment, the temperature is no greater than 125° C. In another embodiment, the temperature is no greater than 100° C. In yet another embodiment, the temperature is no greater than 95° C. In yet another embodiment, the temperature is no greater than 80° C. In one embodiment, the temperature is no greater than 60° C. In one embodiment, the temperature is no greater than 40° C. In one embodiment, the temperature of the system is held constant. In another embodiment, the temperature of the system is increased over time. In another embodiment, the temperature of the system is decreased over time.

In some embodiments, pressure is applied to the system. The pressure can be any pressure that is sufficient to promote the extraction of a lipid from a lipid source and the transesterification of the lipid into a FAME, as would be understood by a skilled artisan. In some embodiments, the pressure is applied by the addition of the second solvent to the system. In certain embodiments, the second solvent is $scCO_2$. In one embodiment, the pressure of the system is between 0.1 MPa and 50 MPa. In another embodiment, the pressure of the system is between 1 MPa and 25 MPa. In yet another embodiment, the pressure of the system is between 5 MPa and 15 MPa. In one embodiment, the pressure of the system is 9.5 MPa. In another embodiment, the pressure of the system is 9.65 MPa. In another embodiment, the pressure of the system is 17.5 MPa. In one embodiment, the pressure of the system is held constant. In another embodiment, the pressure of the system is increased over time. In another embodiment, the pressure of the system is decreased over time. In some embodiments, a gas is added to the system to increase the pressure. Non-limiting examples of a gas include nitrogen and argon.

The systems and methods of the present invention may further include at least one catalyst for transesterification. The present invention is not limited to any particular catalyst or class of catalyst. Although a basic catalyst is not excluded for producing some products, an acid catalyst is preferred, as those techniques avoid the soaps that are formed during base catalysis. Non-limiting examples of acidic catalysts are $H_2SO_4$, $BF_3$, Nafion®, and tungstosilicic acid hydrate. The catalyst may also be a neutral catalyst. Enzymatic transesterification techniques can also be used. In one embodiment, the catalyst is homogenous. In certain embodiments, the catalyst is heterogenous. Examples of heterogenous catalysts include, but are not limited to, Nafion®, tungstosilicic acid hydrate, zeolites, CaO, $K_2CO_3$, hydrotalcite, and mesoporous silica (MCM-41). In a preferred embodiment, the catalyst is Nafion®. In one embodiment, the amount of catalyst loading is between 0.01 to 150 mmol of catalyst per gram of lipid. In another embodiment, the amount of catalyst loading is between 0.1 to 100 mmol of catalyst per gram of lipid. In yet another embodiment, the amount of catalyst loading is between 1 to 50 mmol of catalyst per gram of lipid. In yet another embodiment, the amount of catalyst loading is between 5 to 25 mmol of catalyst per gram of lipid. In certain embodiments, the amount of catalyst loading is 0.36 mmol per gram of lipid. In another embodiment, the amount of catalyst loading is 92 mmol per gram of lipid.

The process of extracting the lipid from the lipid source and transesterifying the lipid into a FAME is carried over a period of time known as the reaction time. As used herein, the term "reaction time" refers to an amount of time effective for the transesterification of at least some lipids into FAMEs. In one embodiment, the reaction time is at least 30 minutes. In another embodiment, the reaction time is at least 1 h. In a certain embodiment, the reaction time is at least 2 hours. In another embodiment, the reaction time is at least 5 hours. In another embodiment, the reaction time is at least 10 hours. In another embodiment, the reaction time is at least 20 hours.

The systems and methods of the present invention provide a highly selective process for the production and isolation of FAME, minimizing the need for additional processes such as downstream separations to remove the FAME from the system, as would be understood by one skilled in the art. In some embodiments, additional methods are used to isolate the FAME from the system. The FAME can be isolated from the system using any method known in the art. In one such method, FAME can be separated from the catalyst by filtration, and can then be separated from solvent by rotary evaporation. If necessary, the FAME can be further purified by any methods known in the art, such as distillation, liquid-liquid extraction, or membrane separations.

Selective Transesterification

The present invention also relates to the selective transesterification of a lipid into a FAME over a different lipid. In some embodiments, within a mixture of lipids, certain lipids can be transesterified into FAMEs while other lipids are not transesterified. In other embodiments, within a mixture of lipids, certain lipids are more favorably transesterified into FAMEs while other lipids are less favorably transesterified into FAMEs. In one such method, this selectivity is due to the selective transesterification of the lipid by a catalyst that selectively transesterifies the desired lipid(s). In one embodiment, the catalyst is Nafion®. The catalyst may be selective for lipids based on the chain length of the lipid. In one embodiment, the catalyst is selective for lipids with chain lengths greater than $C_{18}$. In one embodiment, the catalyst is selective for lipids with chain lengths greater than $C_{12}$. In one embodiment, the catalyst is selective for lipids with chain lengths smaller than $C_{18}$. In one embodiment, the catalyst is selective for lipids with chain lengths smaller than $C_{12}$. The catalyst may be selective for lipids based on the degree of unsaturation per chain of the lipid. In one embodiment, the catalyst is selective for lipids with chain lengths with at least four degrees of unsaturation. In one embodiment, the catalyst is selective for lipids with chain lengths with at least three degrees of unsaturation. In one embodiment, the catalyst is selective for lipids with chain lengths with at least two degrees of unsaturation. The catalyst may be selective for lipids based on the polarity of the lipid. In one embodiment, the catalyst is selective for polar lipids. In one embodiment, the catalyst is selective for non-polar lipids.

Fractionation

The systems and methods of the present invention may further comprise a fractionation step. Using methods described elsewhere herein, in a mixture of lipids, a lipid may be selectively transesterified into FAMEs over other lipids. The properties of the FAMEs may be different as compared to the properties of the non-transesterified lipids, permitting the separation of the FAME from the non-transesterified lipids. In the fractionation step, the FAME is selectively extracted and removed from the system. With fractionation, desired FAMEs can be selectively isolated from the system based on properties of the desired lipids including, but not limited to, polarity, chain length, or degree of unsaturation. Methods of isolating FAMEs are described elsewhere herein.

In some embodiments, the fractionation step may comprise sequential extractions. For example, in a system a first lipid is transesterified into a first FAME in the presence of a second lipid that is not transesterified, and the first FAME is fractionated out of the system while the second lipid remains in the system. After a time, the second lipid is transesterified into a second FAME, and the second FAME is fractionated out of the system. The use of sequential extractions permits the separation of FAMEs with different properties, such as different chain lengths, polarity, or degree of unsaturation, based on the rate at which each FAME is transesterified.

In other embodiments, the fractionation step may be useful for the fractionation of other lipid co-products from the lipid source. Examples of co-products include, but are not limited to non-polar lipids, phospholipids, pigments such as carotenoids, free fatty acids, proteins, and starches. Each co-product may be selectively fractionated out of the system based on factors such as the temperature and/or pressure of the system, the type of solvent(s) within the system, and the properties of the co-product, such as polarity or molecular weight. In some embodiments, $scCO_2$ is a useful solvent for the fractionation of co-products. In one embodiment, in a system comprising a mixture of a first co-product and a second-coproduct and at a first pressure and a first temperature, the first co-product is extracted with $scCO_2$ and fractionated out of the system while the second co-product remain in the system. After a time, the temperature and pressure of the system are adjusted to a second temperature and a second pressure, and the second co-product is with $scCO_2$ and fractionated out of the system. In a further embodiment, an additional solvent is added to the system, and one or more additional co-products are extracted with the additional solvent and fractionated out of the system. In one embodiments, after fractionation of a co-products, the lipid source is further processed within the systems and methods of the present invention.

Reaction System

The systems and methods of the present invention may be carried out within a reaction vessel. A reaction vessel of any size, shape, or internal volume may be used within the systems and methods of the present invention. In some embodiments, the reaction vessel is a reactor. In certain embodiments, the reaction vessel comprises at least one inlet passage and at least one outlet passage. The at least one inlet passage and the at least one outlet passage permit reaction components to enter and/or exit the reaction vessel. In one embodiment, the reaction vessel has a fixed volume. In certain embodiments, the reaction vessel is suitable for performing the reactions described hereinthroughout. Reaction components may be added to a reaction vessel such that the extraction and transesterification reactions may be performed within the reaction vessel. Non-limiting examples of reaction components include a reaction substrate, such as a lipid source, a reaction product, such as a FAME, a solvent, and a catalyst. In one embodiment, a lipid source, a first solvent, a second solvent, and at least one catalyst are added to a reaction vessel, and the extraction and transesterification reactions are performed on the reaction components within the reaction vessel.

Figure 15:
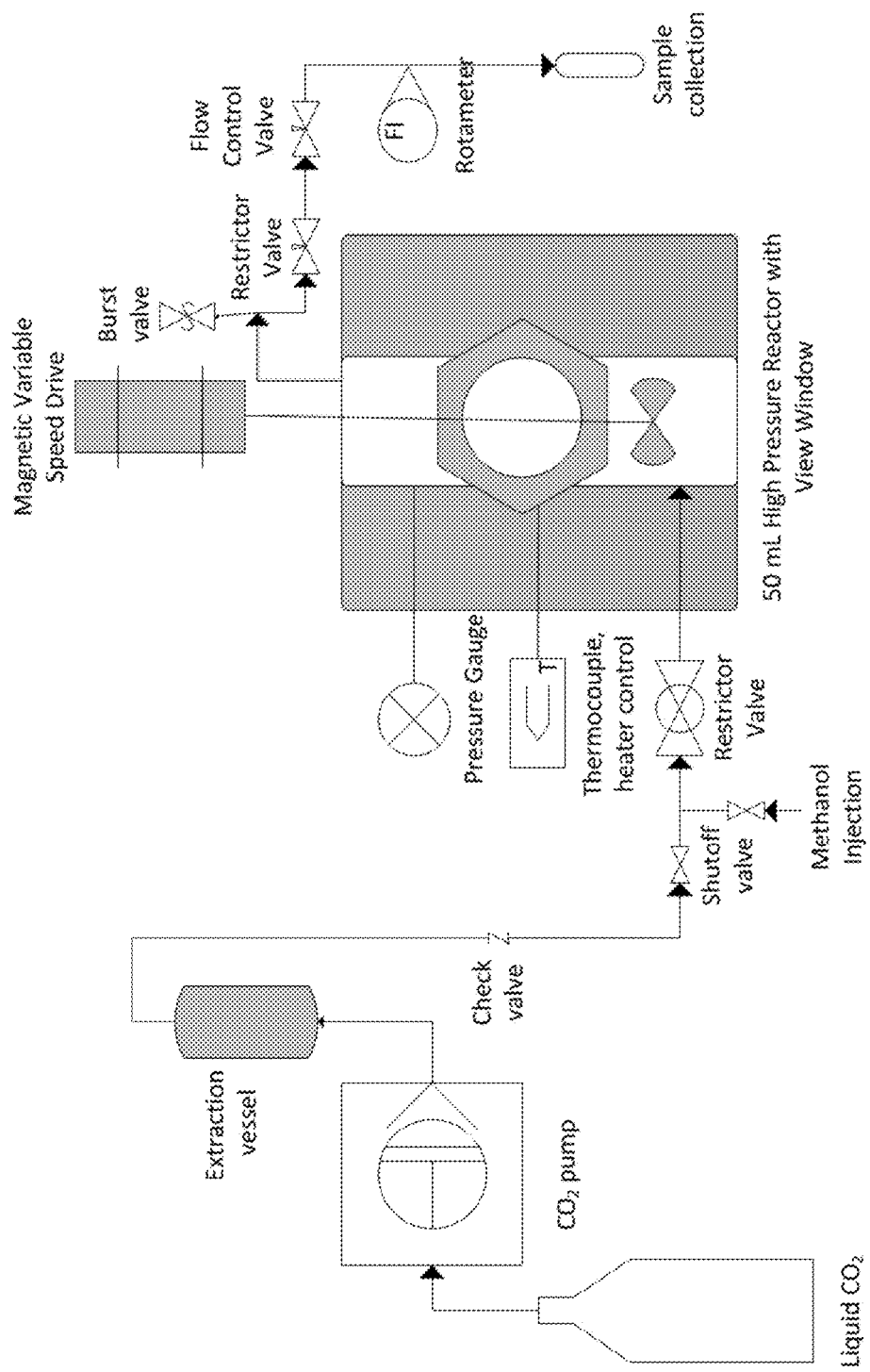
FIG. 15 is a schematic illustrating an exemplary supercritical carbon dioxide, mixed reactor system of the present invention.

In one embodiment, the system comprises a reaction vessel for extracting a lipid from a lipid source and for transesterifying the lipid into a FAME, as referred to in FIG. 15. In a further embodiment, the FAME is fractionated from the reaction vessel. In some embodiments, the system further comprises a thermocouple to adjust the temperature of the system. In other embodiments, the system further comprises a stirring mechanism for stirring the reaction components within the reaction vessel. In other embodiments, the system further comprises a collection vessel for the collection of the FAME and/or an additional product(s) which have exited the reaction vessel. The systems and methods of the present invention may comprise a plurality of reaction vessels. In one embodiment, the system comprises a first reaction vessel for extracting a lipid from a lipid source and a second reaction vessel for transesterifying the lipid into a FAME, as referred to in FIG. 16. In a further embodiment, the FAME is fractionated from the reaction vessel.

According to one embodiment depicted schematically in FIG. 15, the system comprises a high pressure reactor, at least one restrictor valve attached to each of at least one inlet and at least one outlet for controlling the flow of solvent and/or gas into and out of the reactor, a magnetic variable speed drive connected to a stirring rod and paddle to mix the reaction components during the reaction process, and a collection vessel for collection of the FAMEs and/or other product(s) produced during the reaction process. The reactor comprises a chamber that comprises a lipid source, a first solvent, a second solvent, and a catalyst. The lipid source is added to the chamber of the reactor. Methanol is next added to the reactor by injecting methanol into an injection port, flowing through a first restrictor valve and entering the reactor through an inlet. Liquid $CO_2$ is then added to the reactor by first being pumped into an extraction vessel after which it flows through a check valve, a shutoff valve, and a first restrictor valve and enters the reactor. The extraction vessel can preheat and pressurize $CO_2$ before it enters the reactor. The extraction vessel can also extract lipids from biomass, and then the extracted lipids can be added to the reactor. The pressure of the system can be adjusted by varying the amount of $CO_2$ added to the reactor. A pressure gauge provides the pressure of the system. A burst valve is provided as a safety mechanism to relive pressure from the system to prevent an explosion. The temperature of the system can be increased with a thermocouple or a heater control. The reaction components are mixed within the reactor and a lipid is extracted from the lipid source. Upon completion of the reaction, the FAMEs and/or other product(s) exit the reactor by flowing through an outlet, a second restriction valve, and a control valve, and are collected within a collection vessel.

Figure 16:
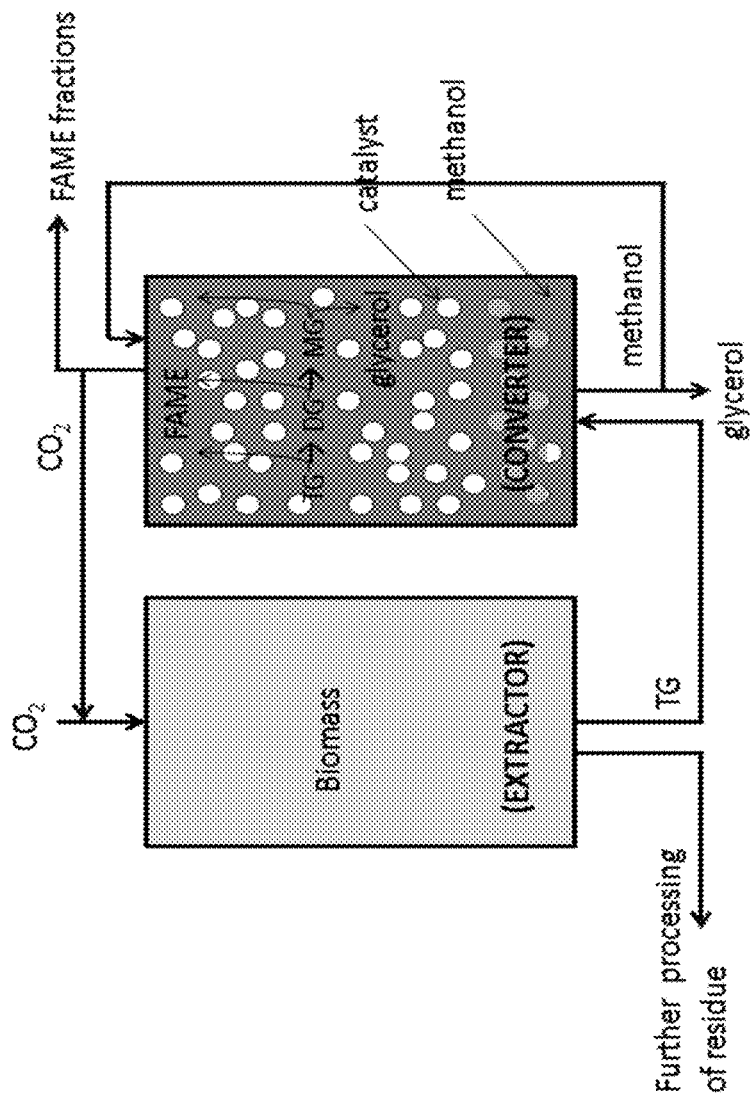
FIG. 16 is a schematic illustrating an exemplary mixed supercritical carbon dioxide reactor system of the present invention.

According to another embodiment depicted schematically in FIG. 16, the system comprises a first reaction vessel for extracting a lipid (the extractor vessel), such as a TAG, from the lipid source, such as biomass, and a second reaction vessel for transesterifying the lipid into a FAME (the converter vessel). The lipid source is loaded into the first reactor, and the lipid is extracted from the lipid source using $scCO_2$ using methods described elsewhere herein. The extracted lipid flows from the first reaction vessel into the second reaction vessel comprised of methanol and catalyst. Additional $scCO_2$ can be added to increase the pressure within the second reactor vessel, and the lipid is transesterified into a FAME using methods described elsewhere herein. Any residue or byproducts remaining in the first reaction vessel can be removed from the first reaction vessel and processed further. The FAME is removed from the second reaction vessel to provide a fraction of pure FAME. Glycerol can also be removed from the second reaction vessel in a separate step.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the systems and methods of the present invention for producing a FAME from a lipid source and practice the claimed methods. The following working examples therefore, specifically point out the preferred embodiments of the present invention, and are not to be construed as limiting in any way the remainder of the disclosure.

Example 1

Advancing More Energy Efficient Biodiesel Production Via Transesterification Using a Mixed Supercritical Carbon Dioxide and Methanol System The materials and methods employed in these experiments are now described.

Materials

All substrates—triolein, diolein, monoolein, methyl oleate, and glycerol—were purchased from Sigma-Aldrich® of at least 99% purity. Methanol was obtained from J. T Baker. Nafion® NR50 was purchased from Ion Power, Inc. Bone dry carbon dioxide with siphon tube and high purity nitrogen gas was supplied by Airgas, Inc. Liquid chromatography solvents (Chromasolv® heptane and isopropanol) were obtained from Sigma-Aldrich® and American Bioanalytical, Inc. respectively.

Supercritical Reactions

All supercritical reactions were performed in a stainless steel 50 mL reactor equipped with a blade stirrer (Parr Instrument Co.) and aligned sapphire windows (FIG. 9) as described previously (Adamsky and Beckman, 1994, Macromolecules 27:312-314). For each reaction, the catalyst and either methanol and substrates (depending on substrate solubility in methanol) were added directly into the reactor, which was then sealed and heated to the desired temperature using four heating irons controlled by a temperature controller monitored by an in situ probe thermocouple. Once the desired temperature was achieved, the other reagent was injected into the system through a two-way valve system. The reactor was then pressurized with $CO_2$ and stirred at 500 rpm. The conditions were maintained for 2 hours after which time the $CO_2$ was vented through heated restrictor and flow control valves. The venting $CO_2$ was slowly sparged through isopropanol for collection. The isopropanol was then poured into the reactor and collected in order to get a fair representation of all reaction substrates. The isopropanol was then sampled and analyzed on LC-MS. All reactions were performed using 10 mg of substrate and 500 mg of Nafion® beads with methyl nonadecanoate used as an internal standard for methanol introduction into the system, and methyl palmitate used as an internal standard for reactor yield recovery. All reactions were performed in at least duplicate.

Cloud Point Measurement

Cloud point measurements were performed in a high pressure, variable-volume view cell using methods previously described (Miller et al., 2010, Energy & Fuels 24:6214-6219). Briefly, the cell consists of a quartz tube housing a floating piston. The sample was loaded directly onto the surface of the floating piston and the mass was determined to within 0.1 mg. Once the apparatus was assembled methanol was then added and the vessel was sealed. $CO_2$ was then introduced into the cell and the system temperature set. The pressure was then increased isothermally by compression of the well-mixed system until the sample was dissolved in the $CO_2$. Once equilibrium was reached, the pressure was slowly decreased by expansion of the vessel volume until a "cloud" of liquid droplets appeared, making the vessel opaque. The point at which this occured was measured and marked as the cloud point. All cloud point measurements were obtained in triplicate. Due to the system design, substrate and methanol loadings were kept at a constant ratio while the amount of $CO_2$ in the system was varied. Though this does not represent a constant "solvent" system, it does represent the effect of methanol loading on the system solubility.

Analysis

Liquid Chromatography/Mass Spectrometry: Analysis of FAME, TAG, DG, and MG was conducted using liquid chromatography—mass spectrometry (Varian 500-MS, 212-LC pumps) with a Waters normal phase, Atlantis® HILIC silica column (2.1×150 mm, 3 µm pore size) with in-line guard column, and Prostar autosampler (20 µL sample loop), and atmospheric pressure chemical ionization. An isocratic elution was done using 9:1 heptane: isopropanol both modified with 0.1% glacial acetic acid at a flow rate of 250 µL/min. APCI conditions were done in positive ion mode with capillary voltage (CV) of 75V, RF loading at 85% with a corona current of +/−5 amps and spray shield voltage of +/−400 V respectively. Quantitative ions were $[M-H]^+$. The method was run for 8 minutes with the following retention times: Triolein 1.6 min; methyl oleate 1.8 min, diolein 2.1 min; monoolein 5.9 min. Mass was estimated by linear regression of standard curve slopes from known standards.

The results of the experiments are now described.

Design of Cloud Point Curves

Due to the highly complex nature of the system attributed to the number of different possible substrates that may be present at varying concentrations at any time during the reaction, a fundamental understanding of the system phase behavior was paramount. For very low substrate concentration, system phase behavior information can be estimated based on the methanol-$CO_2$ binary interaction. While these estimations are informative of the bulk phase behavior, they do not sufficiently reflect the solubility of the substrates (TAG, DG, and MG) in a given phase or mixture. Further, the substrate itself is constantly changing as the reaction proceeds, thereby influencing the solubility of the system components according to the exact conditions (i.e. temperature, pressure, reagent ratios, etc) at any singular time. Thus, cloud point curves were experimentally determined to estimate the solubilities of the different substrates in varying $CO_2$:methanol mixtures. These curves assume the creation of a pseudo-ternary system consisting of methanol, $CO_2$, and substrate, where each potential reaction material (TAG, DG, MG, glycerol, FAME) is isolated as an individual substrate. Phase behavior determination was used to identify appropriate initial system conditions. An experimental design was then developed, varying pressure, temperature, and methanol loading, in order to understand the effect of each parameter in influencing reaction yield and to identify preferred conditions for minimal substrate loading.

Cloud Point Curves

Cloud point curves were determined for the ternary system consisting of reactants or products—specifically triolein, diolein, monoolein, methyl oleate, and glycerol—in mixtures of $CO_2$ and methanol, and were assumed to represent the quantitative measurement for the solubility of the substrate in the mixture.

The known solubilities of the model reactants and products in neat methanol are quite disparate as expected from the varied polarities. Triacylglycerides are nearly insoluble in methanol, but during transesterification step each alkyl chain is exchanged for a hydroxyl group, thus increasing the molecule's polarity (such that polarity of TAG<DG<MG<glycerol). The limited solubility of TAG in methanol (Hegel et al., 2008, Phase Equilibria 266:31-37) limits the ability of the two components to react. On the other hand, glycerol has very limited solubility in $CO_2$ and thus the effect of methanol may increase its solubility, decreasing the efficiency of selecting against this by-product in the product outflow. In order to test the effect of methanol on the system, two methanol loadings were used. The lower methanol loading was a 9:1 methanol:substrate mole ratio, representing a three times stoichiometric excess of methanol. The higher condition (90:1 methanol:substrate mole ratio) was 10× of the low methanol condition. This condition also tested how excess methanol at a relevant concentration affects both the system phase behavior and eventually the reaction yield.

As shown in FIG. 4A, the solubility of the reaction by-product, glycerol, significantly increased at a higher methanol loading; that is, the cloud point lowers appreciably compared to the low methanol and no methanol conditions. Although not wishing to be bound by any particular theory, this difference may be attributed to the effect that methanol has on system polarity. When methanol is exploited as a modifier to $CO_2$, it behaves as a polar co-solvent, and in this case, also as a reactant. For glycerol, a polar molecule, the solubility in non-polar $CO_2$ is very low, but the addition of methanol increases the system polarity and enhances the solubility. It is important to note that the solubility of glycerol remains more than an order of magnitude less than TAG even at the higher methanol loading. However, when operating at higher methanol loadings, it is possible that glycerol could confound product separation and may impede the forward reaction. The other reaction product, methyl oleate, is not pictured, as its solubility is more than two orders of magnitude greater than glycerol.

Figure 4:
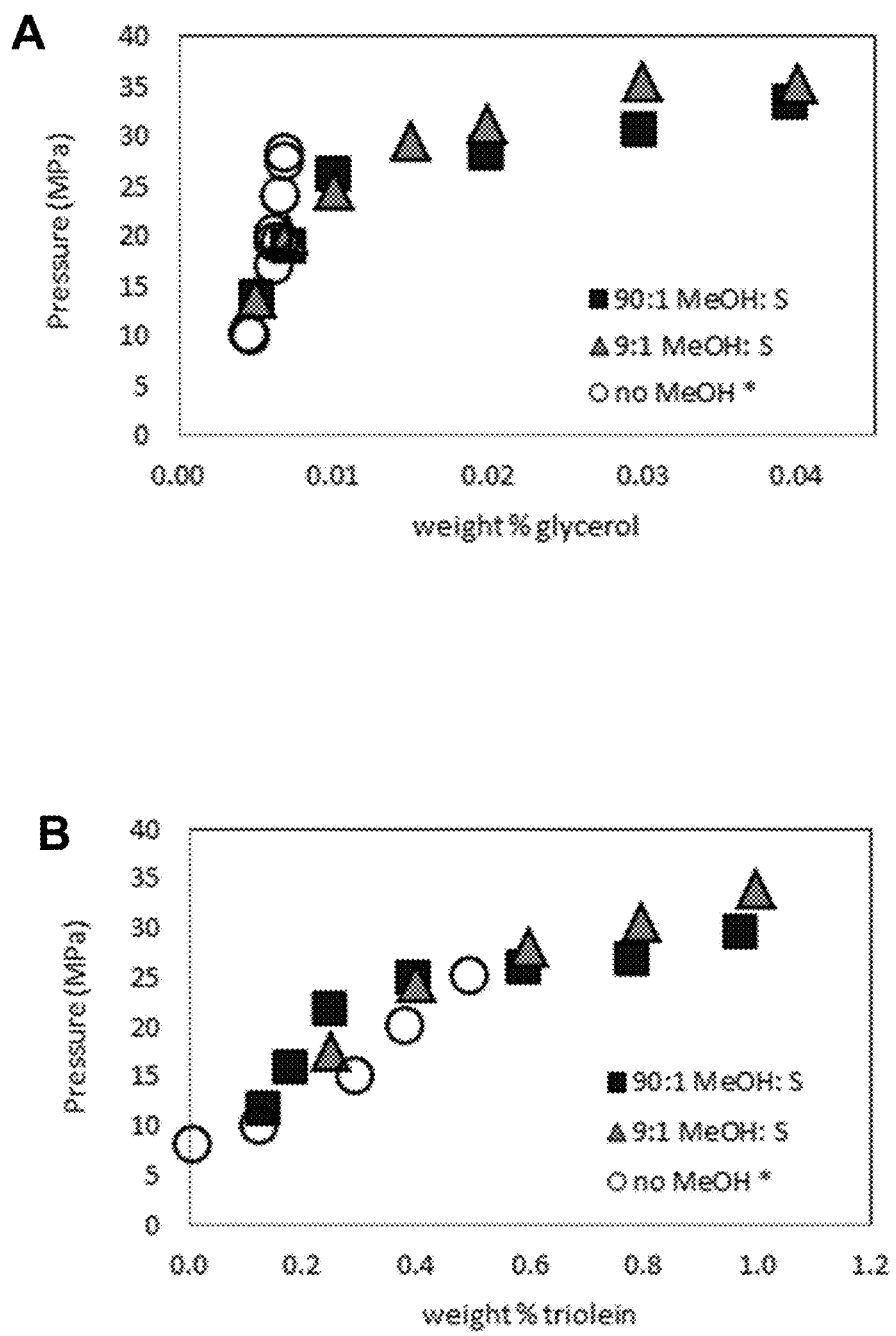
FIG. 4, comprising
Figure 5:
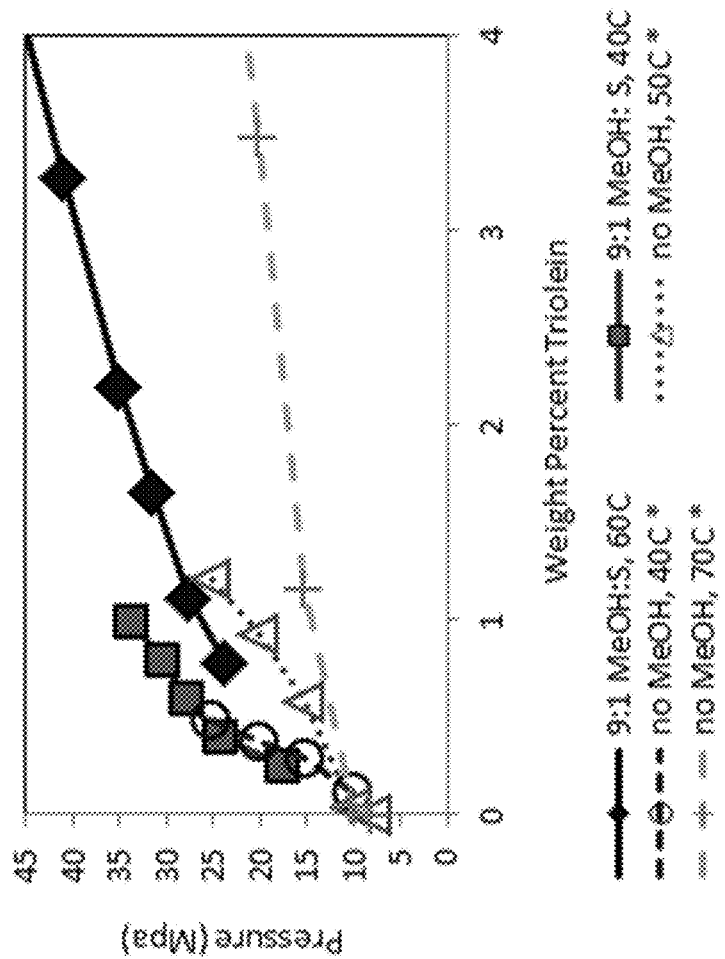
FIG. 5 is a graph illustrating the effect of temperature on the cloud point of triolein with 90:1 methanol:substrate. S=substrate (triolein).

When considering the starting material, triolein, the cloud points do not drastically change as methanol loading is increased (FIG. 4B) when compared to the control, which does not contain methanol. The control system has been previously described (Gupta, 2007, in Solublility in Supercritical Carbon Dioxide, Taylor & Francis Group, LLC). At lower triolein concentrations, methanol seems to have a deleterious effect on solubility potentially due to the poor solubility of triacylglycerides in methanol. This concept was further explored when the effect of temperature and methanol loading on triolein solubility in $CO_2$ was examined. At higher temperatures, methanol directly affected the solubility of triolein within the system. At 40° C., the effect of a 9:1 methanol:triolein ratio does not change the cloud points significantly, but at a higher temperature (60° C.), the cloud points were measured at notably higher pressures (FIG. 5). Although not wishing to be bound by any particular theory, this decrease in solubility of triolein at higher temperature may be attributed to the decreased solvent density, and the fact that methanol and triglcyerides in general are generally insoluble.

Figure 6:
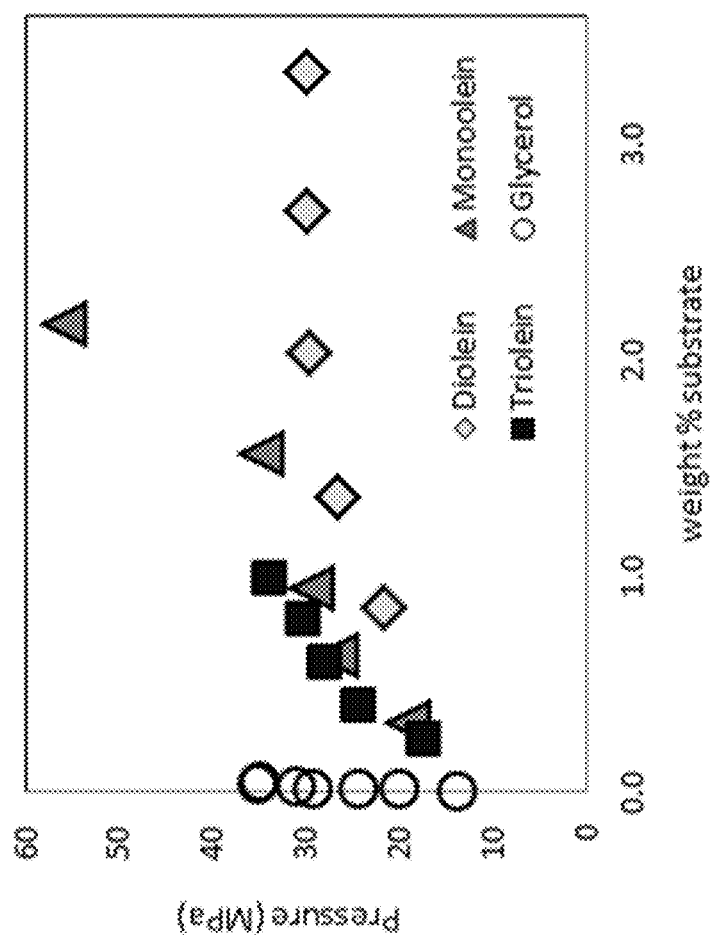
FIG. 6 is a graph illustrating the cloud point curves of each substrate (triolein, diolein, monoolein, and glycerol) with a 9:1 methanol:substrate ratio at 40° C. Methyl oleate is not shown due to significantly higher solubilites. S=substrate (triolein, diolein, monoolein, or glycerol, as specified).

Given the importance of the solubility of the reaction intermediates on phase behavior and reaction kinetics, the effect of methanol in the system on diolein and monoolein was also measured (FIG. 6). Diolein and monoolein are more soluble in methanol than triolein because they are more polar than triolein, and would therefore be more soluble in a polar solvent such as methanol. This increased solubility of the system intermediates should drive the equilibrium toward products because the intermediates are more likely to remain in solution. Otherwise, if the intermediates became isolated from the reaction medium, the equilibrium would likely be shifted backward toward starting materials, reducing the conversion of starting materials and intermedates to the desired products. Bubble points (first point where a vapor bubble appears) for all of the conditions tested did not significantly change between substrates and were measured to be ~7.6 MPa.

Experimental Examination of Pressure, Temperature, and Methanol Loading

The initial cloud point results indicated that the reactant solubilities in $scCO_2$ with methanol were favorable for the forward reaction, and also provided information as to which conditions to survey for supercritical reaction. Two conditions signifying low and high values for each parameter of pressure, temperature, and methanol loading were selected (Table 1). Temperatures were chosen with the goal of minimizing the energy intensiveness of supercritical transesterification. 40° C. is just above the critical temperature of $CO_2$ but high enough to allow for a single phase of methanol and $CO_2$ to be produced at certain pressures and methanol loadings. 80° C. is high enough for significant catalytic reaction at ambient conditions to occur, yet still allows for the determination of increased or decreased reactivity in the supercritical system.

TABLE 1

Summary of Reaction Conditions

| # | P Mpa | T ° C. | Vol. MeOH mL | No. of phases* | Mixture density g/mL** | Weight percent | | |
|---|---|---|---|---|---|---|---|---|
| | | | | | | $CO_2$ | MeOH | Substrate |
| 1 | 9.5 | 40 | 0.35 | 1 | 0.657 | 99.0 | 1.0 | 0.034 |
| 2 | 9.5 | 40 | 1.8 | 1 | 0.759** | 95.1 | 4.9 | 0.034 |
| 3 | 9.5 | 80 | 0.35 | 2 | 0.228 | 97.3 | 2.6 | 0.096 |
| 4 | 9.5 | 80 | 1.8 | 2 | 0.275 | 87.3 | 12.6 | 0.089 |
| 5 | 17.5 | 40 | 0.35 | 1 | 0.821 | 99.3 | 0.7 | 0.025 |
| 6 | 17.5 | 40 | 1.8 | 1 | 0.838 | 96.5 | 3.5 | 0.030 |
| 7 | 17.5 | 80 | 0.35 | 1 | 0.547 | 98.9 | 1.1 | 0.039 |
| 8 | 17.5 | 80 | 1.8 | 1 | 0.615 | 94.6 | 5.4 | 0.042 |

* As obtained from Reighard et al., 1996, Fluid Phase Equilibria 123: 215-230
**Calculated from REFPROP for $CO_2$-methanol binary (Lemmon and McLinden, 2010, National Institute of Standards and Technology - Standard Reference Data Program, Gaithersburg)
***Not calculated to be above the critical point of the mixture Regarding system pressure, 9.5 MPa was selected as the low pressure parameter, because it provided a region where a two-phase system could be tested at 40° C. The upper pressure of 17.5 Mpa was selected because the methanol-$CO_2$ binary system would exist as a single phase at both 40° C. and 80° C. Methanol loadings were selected to be roughly 0.5 wt % and 4 wt % because these values fall into the range of total system methanol loadings (as reflected in the 9:1 and 90:1 methanol:susbtrate cloud point curves, respectively; FIGS. 4-6). Because the volume of the reactor is fixed, varying the pressure and temperature directly affected the ratio of methanol to carbon dioxide as well as the density of the system when the amount of methanol added at ambient pressure to each test condition remained constant.

Examination of Catalysts

Two heterogeneous, commercially acquired catalysts, zeolite and Nafion®-NR50, were evaluated. The use of zeolite, despite its fast and complete yields at ambient pressures, was not successful and in fact promoted the transalkylation in the reverse direction, whereby the monoglyceride was converted to both DG and TAG. In contrast, the use of Nafion® looked more promising at more desirable temperatures.

Figure 7:
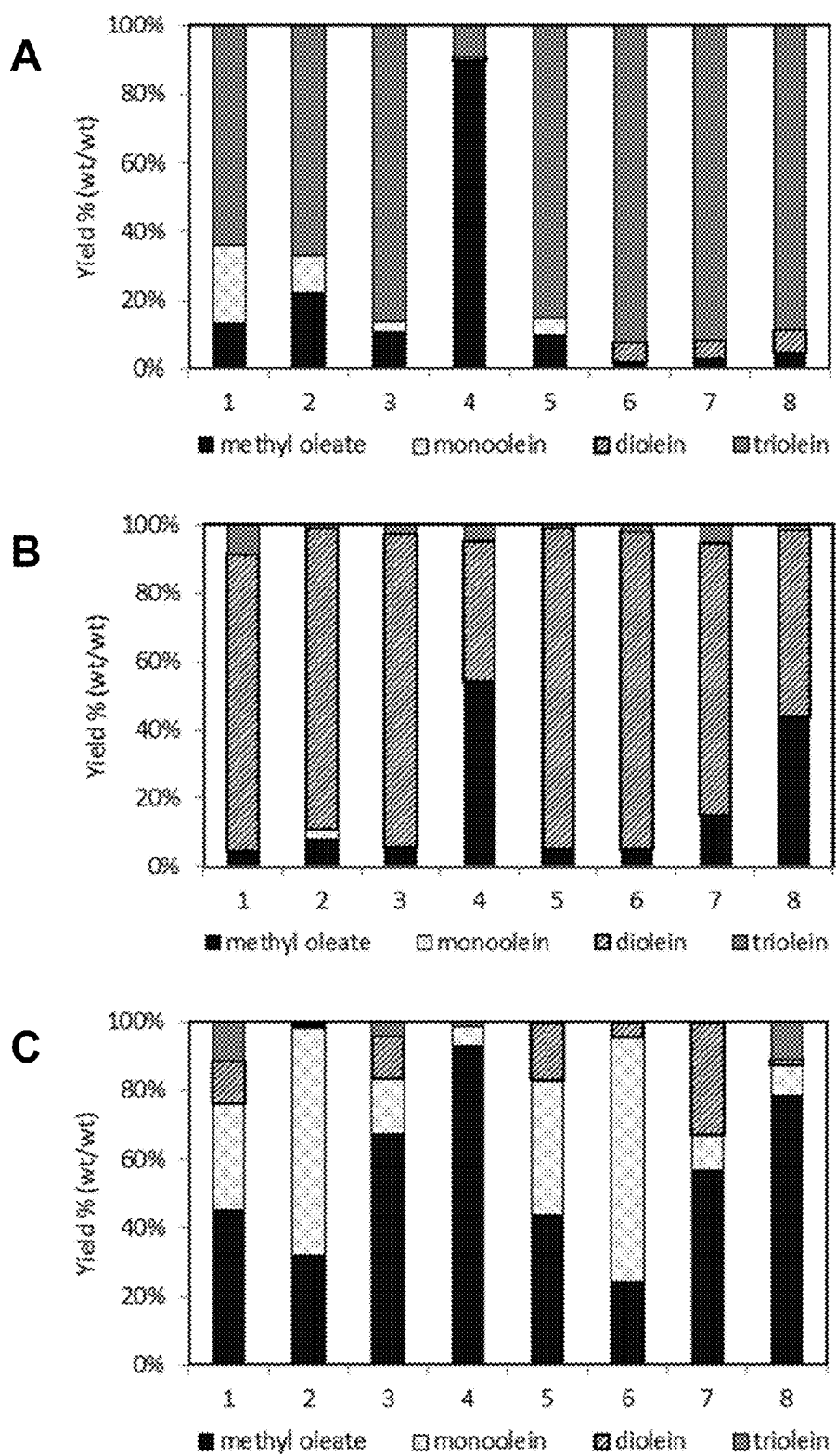
FIG. 7, comprised of FIGS. 7A-7C, illustrates the results of experimental conditions for transesterification, as tested herein using carbon dioxide, methanol, and catalyst at temperatures and pressures above the critical point of carbon dioxide (Table 1).

The results of the experimental matrix using Nafion® as the reaction catalyst can be seen in FIG. 7A. Conditions yielding a high amount of FAME from the transesterification of triolein ocurred at 80° C. and 90:1 methanol:triolene loading, but performing the reaction at the lower pressure of 9.5 MPa yielded ~93% (wt/wt) methyl oleate [conditions included 1.8 mL methanol (3.6% $v/v_{reactor}$, ambient), 80° C., 9.5 Mpa, Entry 4 of Table 1]. Compared to the other seven conditions tested, this yield is signficantly higher and occurs at a point where methanol and $CO_2$ are expected to be in two phases (Table 1). Under these conditions, the methanol loading is higher when normalized to the weight of the other reactor components (~12.6 wt % compared with the next highest of 5.4%, Table 1, Entry 4). Although not wishing to be bound by any particular theory, this result suggests why the increased yield is observed, but other factors must also contribute to the high yield as this amplification is not observed to the same extent when starting with monoolein or diolein, nor during designed control experiments.

Importance of $CO_2$ in the Reaction

A control experiment was performed in the absence $CO_2$ to determine whether $CO_2$ offers a unique benefit to the system performance, and also to rule out the possibility that the increased yields are due an enhanced reaction rate resulting from the increased pressure and temperature of the system. The reaction was repeated using previously identified preferred conditions (Table 1; Entry 4), except $CO_2$ was substituted with nitrogen gas. The yield of this reaction was less than 5%, indicating that $CO_2$ has an important function in the reaction and that the reaction cannot be driven by high pressure and temperature alone. Although not wishing to be bound by any particular theory, it was hypothesized that $CO_2$ may be changing the availability of triolein to methanol by either changing the solubility of triolein in the system mixture and/or changing the phase behavior and system properties.

Determination of the Rate-Limiting Step of the Transesterification

The roles of the intermediates DG and MG within the transesterification reaction were examined in order to determine both the reaction limiting steps and the effect of the intermediates on solubility within the supercritical reaction (FIGS. 7B and 7C). When the diolein is used as starting material (specifically a mixture comprising 75% of 1,3- and 25% of 1,2-dioleoylglycerol, conditions listed in Table 1; Entry 4), the yields of methyl ester are significantly less than when triacylglyceride is used as starting material under identical reaction conditions (FIG. 7B). Although not wishing to be bound by any particular theory, this suggests that under these system conditions, the rate limiting step is the conversion of diglyceride to monoglyceride.

Theoretical calculations of the activation energies for acid-catalyzed transesterification of TAG show that the energy barrier for transesterification of 1,2-DG to an MG is greater than energy barrier for transesterification of TAG to DG. However, these calculations also show that the energy barrier for transesterification of 1,3-DG to MG is only slightly less than energy barrier for transesterification of TAG to DG (Asakuma et al., 2009, Fuel 88:786-791. Because the diolein mixture is comprised of only 25% 1,2-DG, and based solely on activation energy, a 25% reduction in yield would be expected for the reaction. The actual yield decrease is closer to 40%, and thus the difference is likely not due to the energy barrier for transesterification of 1,2- vs. 1,3-diolein, but rather another factor. Also observed were small amounts of the reverse reaction, which is the conversion of diolein to triolein. The best yields for the production of methyl oleate from diolein were seen with high methanol loading at 80° C., and were less dependent on pressure than results from using triolein as the starting material under the same conditions.

Unexpectedly, when monoolein was used as the starting material, the yields of methyl oleate production were higher than when either TAG or DG were used as starting materials (FIG. 7C). From an activation energy perspective, the MG was predicted to have had a larger thermodynamic barrier for transesterification than the TAG (Asakuma et al., 2009, Fuel 88:786-791), but the results when using $CO_2$ under the higher pressure do not support this hypothesis. Although not wishing to be bound by any particular theory, these high yields of FAME may be attributed to favorable phase behavior and/or solubility, which would provide better access of methanol and catalyst to the MG. The high yield for monoolein was similar to that when triolein was used as the starting material (Table 1; Entry 4), although high yields were also observed under high pressure conditions at the same temperature and with identical methanol loadings. This trend was similar to the results observed when diolene was used as starting material.

Phase Behavior Under Preferred Reaction Conditions

Figure 8:
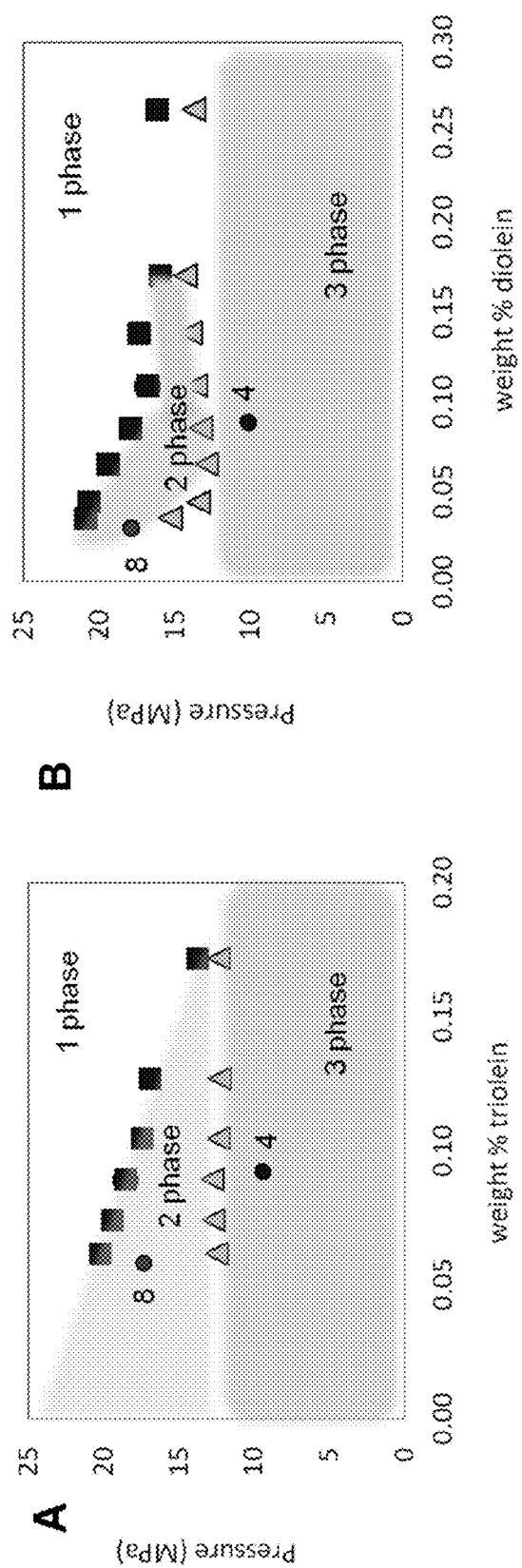
FIG. 8, comprising

Preferred conditions for the transesterification reaction within this highly complex system were found to be 80° C. with 90:1 methanol:substrate loading and at the lowest tested pressure (9.5 MPa). In a simplified binary system consisting of methanol and $CO_2$ existing under these preferred conditions, the methanol and $CO_2$ do not form a single phase (Reighard et al., 1996, Fluid Phase Equilibria 123:215-230), but instead form a binary phase comprising an expanded methanol phase ($CO_2$-rich methanol) and a methanol-rich $CO_2$ phase. Cloud point and bubble point curves (FIG. 8) were experimentally measured to further study phase behavior under preferred conditions (Table 1; Entry 4). When triolein was used as the starting material substrate, the results demonstrated that at all of the lower pressure conditions tested, these systems exist below both the cloud point and bubble point (FIG. 8A) and therefore exist in at least two phases. It was next examined whether or not the triolein, which is not normally soluble in methanol, is soluble in one of these phase, and in which phase the triolein is partitioned.

Figure 9:
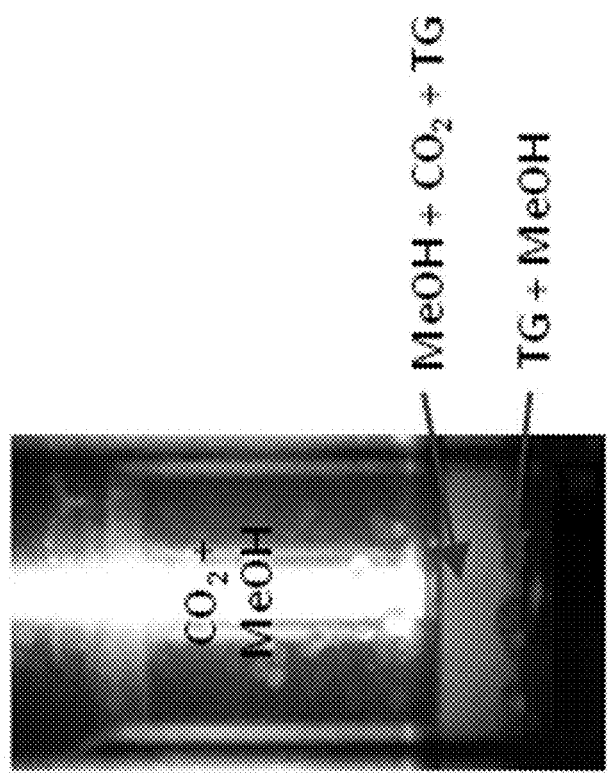
FIG. 9 is a photograph illustrating the ternary-phase system in variable view cell under 80° C., 9.5 MPa and with 12.6% methanol loading. The photograph reflects the fluid phase behavior and does not capture the actual reactor, which would also include the solid catalyst.

The fluid phase behavior of triolein, methanol, and $CO_2$ (excluding catalyst) in the variable-view cell is depicted in FIG. 9. At preferred system conditions, (Table 1, Entry 4) three phases exist and the conditions are below the bubble point of the methanol-triolein-carbon dioxide ternary system. The phases consist of an upper phase composed of methanol-rich $CO_2$, and two lower phases: a $CO_2$-rich methanol phase and methanol-rich triolein phase. Contact between the triolein and methanol only occurs in the lower phases. Although not wishing to be bound by any particular theory, it was hypothesized that $CO_2$ was acting as a co-solvent in the transesterification reaction between methanol and TAG by increasing the solubility of TAG in the methanol, thus resulting in the observed high yields of FAME.

$CO_2$ as a Co-Solvent

It was hypothesized that substituting $CO_2$ with an alternative co-solvent in the reaction system should not affect product yield if indeed the observed high reaction yields were simply due to a solubility effect, wherein an increase in the solubility of trioleine in the reaction system enhances the reaction. A control experiment was conducted under preferred conditions (Table 1; Entry 4) where $CO_2$ was substituted with nitrogen gas and ethyl acetate was added as a co-solvent with methanol. The results showed an increase in methyl oleate yields from below 5% (as observed in the previously described experiment when only $CO_2$ was substituted with nitrogen gas) to above 50%. Therefore, a co-solvent, which increases solubility of the substrate in the reaction, was determined to be a necessary component of the transesterification reaction. However, these results do not fully explain the superior results observed for the $CO_2$-MeOH system at 80° C., 9.5 MPa, and 3.6% methanol (v/v$_{reactor}$, ambient) loading.

As with carbon dioxide, ethyl acetate to some extent facilitates the interaction between methanol and triolein within the system. The increased pressure (as compared to ambient pressure) is also required for reactivity, as previously conducted experiments using ethyl acetate and methanol at ambient pressures resulted in reduced yields. The yield of product using the $CO_2$-methanol system is still far greater than the yield of product using the ethyl acetate-nitrogen-methanol control, supporting the hypothesis that the properties of $CO_2$ are critical to the overall properties of the $CO_2$:methanol co-solvent system. Although not wishing to be bound by any particular theory, because the yield of product from the carbon dioxide-methanol system is higher than the yield of product from the ethyl acetate-nitrogen-methanol system under otherwise identical conditions, the superior yield of the carbon dioxide-methanol system may be due to either the different solubilities of each reaction substrate (e.g., starting materials, intermediates, products) driving the reaction forward and/or local composition effects of methanol surrounding the substrate (Ellington et al, 1994, Ind. & Eng. Chem. Res. 33:965-974). Different solubilities for each reaction substrate may contribute to the reaction yields, and may also provide a simplified method of separating the biodiesel product from the glycerol by-product.

The cloud point and bubble point curves of diolein indicate that under the preferred reaction conditions (Table 1; Entry 4), the system is below the bubble point of the mixture and three phases exist (FIG. 8B). When the system is comprised of a pressure of 17.5 MPa and a temperature of 80° C. (Table 1, Entry 8; FIG. 7B, Point 8) the system is above the bubble point yet below the cloud point of the mixture and thus exists in two fluid phases. As discussed elsewhere herein, when diolein is used as starting material under either of these reaction conditions, the yields of product were similar. Therefore, it was observed that the reactivity of dieolein is only affected by temperature and pressure, and is not dependent upon the number of phases of $CO_2$ and methanol in the system. Although not wishing to be bound by any particular theory, this result may be explained by the fact that diolein is more polar than triolein, and that the interaction between diolein and the methanol (a polar solvent) is not significantly affected by the presence of $CO_2$ in the system. Rather, it appears that it is the polarity of the substrate, as opposed to the co-solvent, that determines the effect $CO_2$ has on the system.

Although not wishing to be bound by any particular theory, because diolein is more polar than triolein, it is hypothesized that diolene will have a higher inherent solubility, and thus reactivity, in methanol. Monoolein, the most polar of the the reaction substrates, is highly soluble in methanol, and therefore it is hypothesized that the concentration of $CO_2$ in the system (as determined by system pressure) should therefore not have any effect on the yields of FAME in the transesterification reaction. Indeed, the observed results support this hypothesis, because at all experimental conditions tested, the highest observed yield of methyl oleate produced from monoolein occurred under reaction conditions with the highest temperature (80° C.) and highest methanol:substrate loading (90:10, FIG. 7C). High reactivities of monoolein are essential to minimize the contaminanting amounts of MG in the fuel product (ASTM, 2011, in D6751-11b, Vol. D6751-11b).

Surface Methodology Model

In order to further improve the reaction yields, a surface methodology model was generated for the system. The experimental results were fit to a two-level factorial design regression model. The effects of the three experimental variables (pressure, temperature, and methanol loading) as well as the effects associated with their interactions were estimated taking into account the total yield at the high and low values for each factor (Myers et al., 2009, from Response Surface Methodology: Process and Product Optimization Using Designed Experiments, John Wiley & Sons). From these calculated effect parameters, a regression model was calculated with n=7 variables associated with each of the 3 factors and 4 interactions. The model had an $R^2$ value of 0.75 and was found to provide information which may be useful for the design of improved system conditions.

Figure 10:
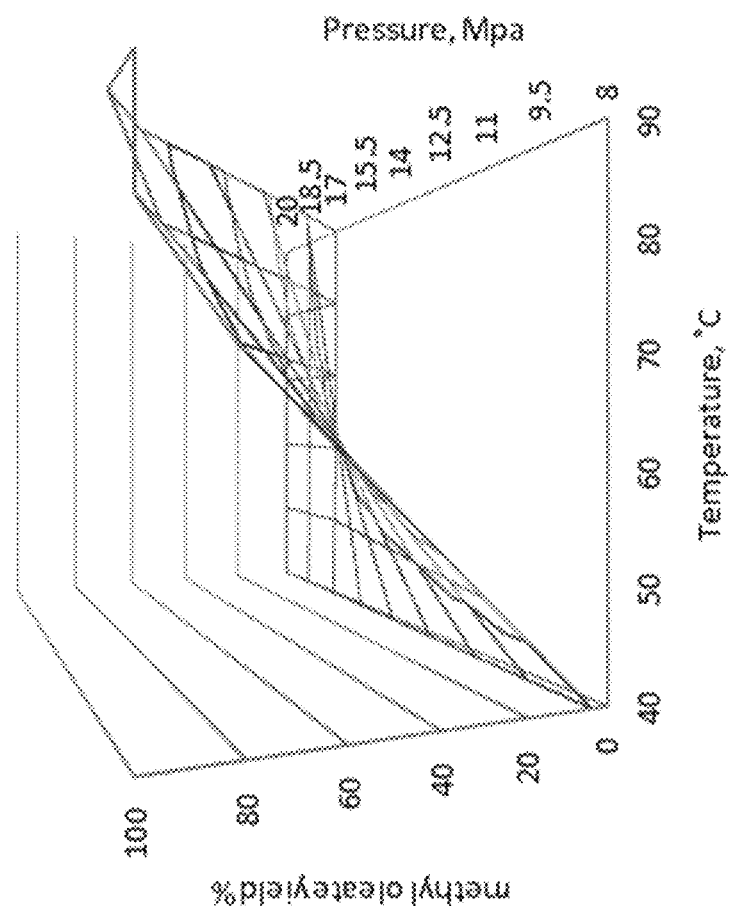
FIG. 10 is a graph illustrating surface methodology model results for methyl oleate obtained in >90% yield from triolein under mild conditions in a mixed $CO_2$/methanol system. Starting reaction conditions: 1 g/L triolein, Nafion®NR50 (92 mmol catalyst/g substrate), 3.6% methanol (v/v$_{reactor}$, ambient), 2 h.

The data provided by the model studies suggested that the experimental variable with the largest impact on FAME yield is pressure. However, the model studies also found that all three experimental variables (pressure, temperature, and methanol loading) and their interactions exerted a significant effect on the yield of FAME. That these parameters and interactions provide significant contributions to the yield of FAME is not surprising as they all contribute to system density and phase behavior, which are closely related and difficult to separate from each other. The results seen in FIG. 10 represents the yield of methyl oleate from the transesterification of triolein when pressure and temperature are varied and the methanol volume is kept at a constant value [the preferred level of 3.6% methanol (v/v$_{reactor}$, ambient)].

The surface model indicated that a slight increase in temperature may increase the reaction yield to close to 100%. To validate the model and this finding in particular, the same pressure and methanol loading (9.5 MPa, 1.8 mL methanol) as the preferred reaction condition (Table 1, Entry 4) was evaluated, however the temperature was increased from 80° C. to 95° C. The resultant yield of FAME under these conditions was 98.3%. This result supported the hypothesis that this model may be useful for the development of improved reaction conditions.

Energy Calculations

The low-temperature system for the production of biodiesel described herein has significant additional energy advantages over systems currently in use. When considering the use of primary reactor alone, a change in temperature from 250° C. to 95° C. reduces the theoretical minimum heating requirements of the methanol from 0.68 to 0.21 kJ/g of substrate processed, resulting in a decrease of nearly 70%. This calculation assumes a specific heat capacity of methanol of 61.4 J mol$^{-1}$ K$^{-1}$ and a molar ratio of methanol to TAG of 42:1, and is independent of pressure as the methanol is injected into the reactor at the desired temperature once the $CO_2$ has reached a supercritical state. Although not wishing to be bound by any particular theory, this molar ratio of 42:1 methanol:TAG suggests the use of methanol levels well in excess of stoichiometric requirements. Lowering the molar ratio of methanol to TAG in the current system may provide further reductions in energy requirements. Other energy considerations include the water content of the input algae slurry from commercial-scale wet processing and energy requirements for $scCO_2$.

System for Transesterification

In some instances, the concentration of TAG and the amounts of methanol loading, catalyst loading, and/or reaction kinetics are modified for large scale processing. Yields may also be improved by using a Nafion® catalyst with an increased surface area, The system phase behavior may be improved to provide the desired/required levels of each system component and the best means to isolate the fuel product. Although these experiments have focused on the use of oleate substrates, the substrate chain length and degree of unsaturation of the fatty acids may be varied for use within the system described herein. Mixed substrates may also be used within this system.

The system may operate in a continuous flow-through process for commercial-scale conversion. A continuous flow model of the system described herein may aid in the improvement of a commercial-scale system as well as in the sizing of equipment for a pilot reactor.

The triacylglycerides used within the system described herein may come from a number of different biological feedstocks, under moderate temperature and pressure. The system described herein may be useful in a one pot method comprised of the extraction of triacylglycerides from lipid-rich feedstocks and subsequent conversion of the triacylglycerides into biodiesel. The combination of supercritical extraction of wet biomass with the system for transesterification described herein may be highly energetically favorable and provide sustainably-produced biodiesel.

Example 2

Figure 11:
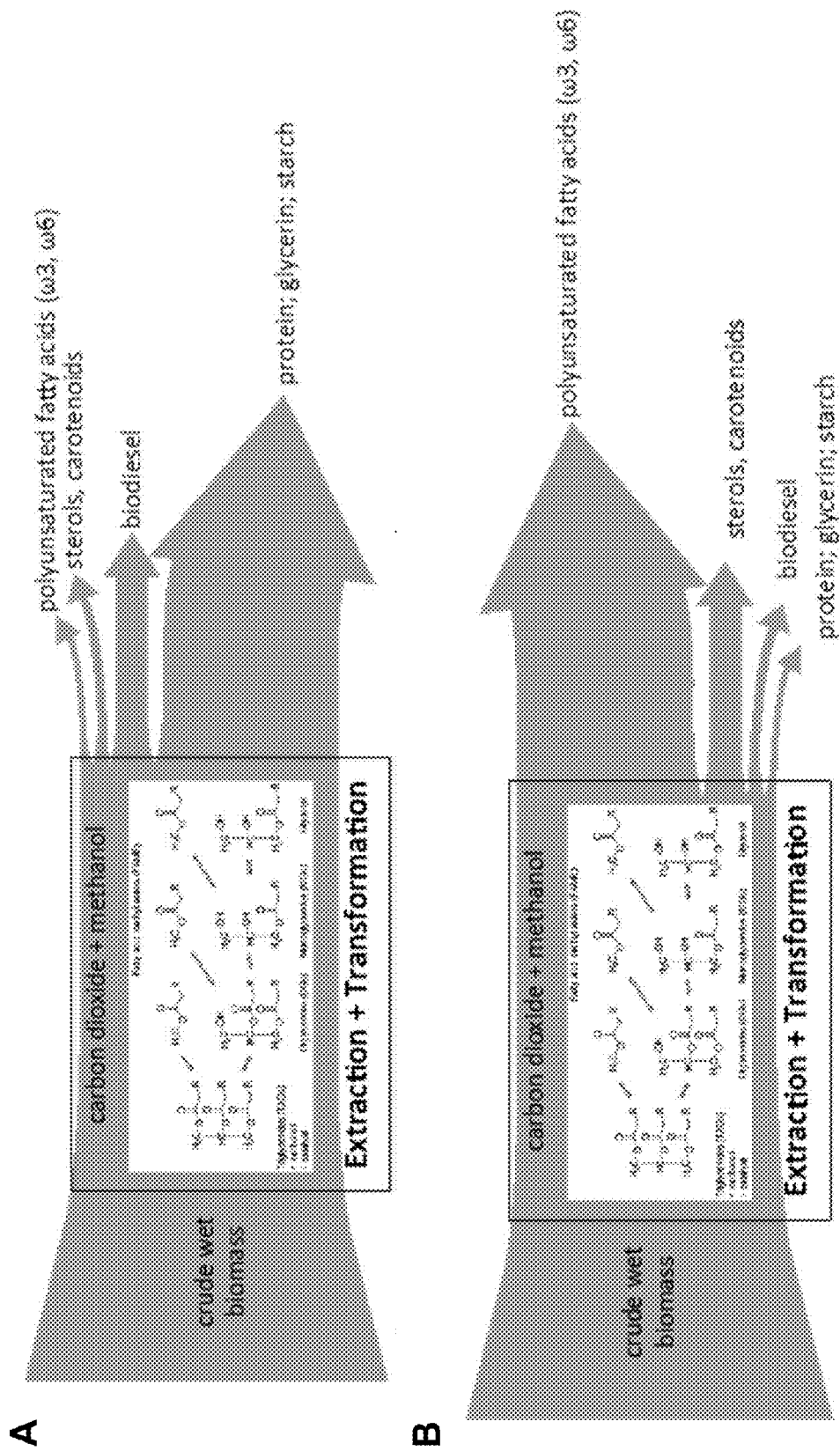
FIG. 11, comprised of FIGS. 11A-11B, illustrates an overview of the biorefinery concept.
Figure 17:
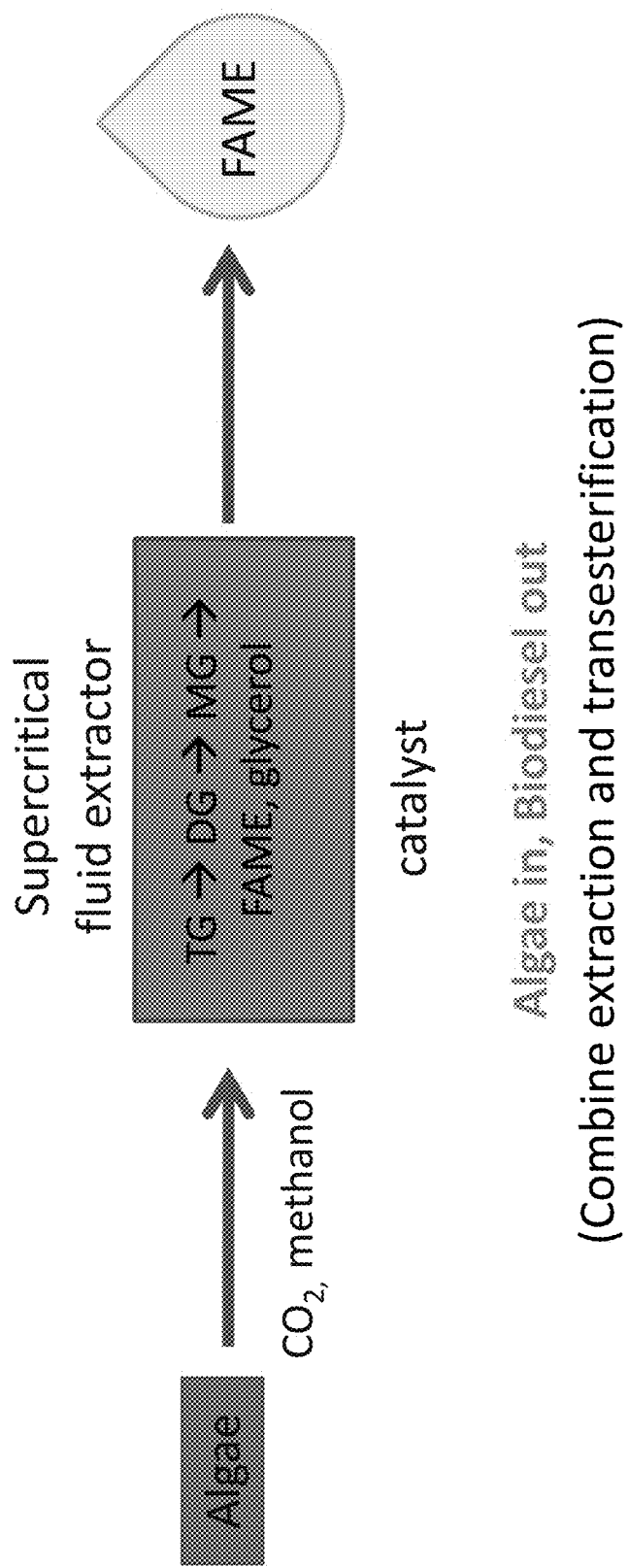
FIG. 17 is a schematic illustrating an exemplary extraction and transesterification system of the present invention.

Isolation, Fractionation, and Transformation of Biobased Feedstocks into Fuels and Chemical Products Described herein are studies directed toward the examination of system variables for extraction, fractionation and transformation of wet biomass using a supercritical carbon dioxide:methanol mixture (FIG. 17). Also described herein are methods for systematically and quantitatively measuring and modeling phase behavior to guide the improvement of the overall system. The differential solubility of TAGs and their transesterification intermediates in $CO_2$-methanol systems in the presence or absence of water is examined. The evaluation of selective extraction, fractionation, and transformation of dry biomass is also examined by exploring catalyst effects on differential conversion and fractionation of model compounds. These processes are successfully demonstrated on freeze-dried crude biomass samples. This extraction and transformation processes is extended to include wet biomass, with the development of reaction conditions guided by the phase behavior models and understanding of catalyst activity (FIG. 11). The results of these biomass studies may be useful as the basis for a techno-economic analysis to determine how a biorefinery operation might improve a portfolio of fuel and nonfuel-based products while considering improved system performance and variable market dynamics.

Analysis

TAG, DG, MG, glycerol, and FAME are quantified through the use of liquid chromatography-mass spectrometry (LC-MS) with atmospheric pressure chemical ionization (APCI). Mass spectrometry permits the identification of these compounds by both retention time and molecular weight. FAME, as well as monoglyceride, diglyceride, and triacylglyceride standards, is successfully separated using heptane as the elution solvent using previously described methods (Soh and Zimmerman, 2011, Green Chem. 13:1422-1429). The column used is a normal phase hydrophilic interaction liquid chromatography (HILIC) column (Waters) at a flow rate of 0.25 mL/min. Mass spectral settings were calibrated for FAME with short, medium, and long chain lengths at capillary voltages of 75 and 110V, and RF loadings of 80% and 95%, respectively. Using this method, reaction substrates are identified and quantified, and lipid profiles of crude biomass extracts are assessed for fatty acid chain length and degree of unsaturation in addition to the amount of contamination. Similarly, other lipid fractions, including carotenoids, can be evaluated on the LC-MS using previously described methods (Rodriguez-Bernaldo de Quirós and Costa, 2006, J. Food Composition Anal. 19:97-111).

Phase Behavior Determination

The phase behavior of substrates and reaction mixtures is measured in a variable volume, high-pressure view cell (D. B. Robinson and Associates; Edmonton, Alberta, Canada) using methods previously described (Lepilleur and Beckman, 1997, Macromolecules 30:745-756; Potluri et al., 2003, Fluid Phase Equilib. 211:211-217). Cloud point curves are measured isothermally. Methanol (or methanol/water) and substrate are added to the cell at a pre-determined ratio and the system is subsequently sealed. Once the desired temperature is achieved, a measured quantity of $CO_2$ is added at 11 MPa at room temperature (23° C.) isothermally. Once the desired amount of $CO_2$ is added, the cell pressure is increased (up to 55 MPa) until all components are dissolved and a single phase is formed. The cell is mixed at this pressure until equilibrium is achieved, then depressurized until the cloud, dew, and bubble points are observed.

Modeling

The systems under consideration contain $CO_2$, methanol, water, TAG, DG, MG, FAME, and/or glycerol. The large number of components of the system complicates the task of modeling phase behavior because these components include chain-like molecules, highly compressible fluids, and hydrogen bond donors and acceptors. The well-known Statistical Associating Fluid Theory (SAFT) (Huang and Radosz, 1990, Ind. Engl. Chem. Res. 29:2284-2294; Huang and Radosz, 1991, Ind. Engl. Chem. Res. 30:1994-2005) is employed which has been shown to provide accurate descriptions of complex mixtures similar to this system because of SAFT's ability to account for non-spherically shaped molecules, attraction and repulsion between molecules, and site-site interactions. The SAFT model is based upon an equation of state (Eq.1) that splits the Helmholtz free energy into two terms, the reference and perturbation contributions. The reference part includes the hard sphere, chain, and association contributions, while the perturbation term incorporates the mean-field dispersion effects. The SAFT reference term equation is given by:

$$\frac{a^{ref}}{RT} = \frac{a^{hs}}{RT} + \frac{a^{chain}}{RT} + \frac{a^{assoc}}{RT} \quad \text{(Eq. 1)}$$

where the terms on the right include the hard sphere, chain formation, and association terms. The perturbation part of the free energy is modeled as a power series (Alder et al., 1972, J. Chem. Phys. 56:3013-3029), which incorporates the pure component dispersion energy. For non-associating systems, the SAFT equation of state includes three parameters for each component, the segment number (m), the temperature-independent segment volume ($v^{oo}$), and the temperature independent segment energy $\mu/K$. For mixtures, the dispersion cross-interaction term is generated via the geometric mean of the pure component parameters plus an interaction term ($k_{ij}$). In associating systems, Wertheim's expression for the association strength is employed:

$$\Delta = \kappa\left[\exp\left(-\frac{H}{\kappa T}\right) - 1\right]\rho g^{(\sigma)} \quad \text{(Eq. 2)}$$

where $g^{(o)}$ is the pair correlation function at contact; p, the bulk fluid density; H, the enthalpy change on hydrogen bond formation; k, Boltzman factor; T, temperature; and $\kappa$ is the bonding volume. For cross-associations (hydrogen bonding) a simple geometric mean for $H_{ij}$ and $K_{ij}$ may be employed although the latter is modified by an interaction term $a_{ij}$ (Suresh and Beckman, 1994, Fluid Phase Equilib. 99:219-240). If a pure component parameter has been acquired through fitting of the SAFT model to single component pressure-volume-temperature (pVT) data or vapor-liquid equilibrium (VLE) data, binary mixtures can be modeled using two adjustable parameters, $a_{ij}$ and $k_{ij}$. A decision is made as to which of the species present can associate in solution. In the case of methanol-$CO_2$-TAG, and without wishing to be bound by any particular theory, it is hypothesized that methanol self-associates (methanol possesses one hydrogen bond donor and one hydrogen bond acceptor) and that methanol can cross-associate with the TAG (TAG possesses three hydrogen bond acceptors by way of the carbonyl oxygen atoms). It is hypothesized that $CO_2$ does not form hydrogen bonds with low molecular weight alcohols. SAFT permits the use of a good description of $CO_2$-methanol phase behavior without the need to incorporate hydrogen bonding interactions between the $CO_2$ and methanol.

Modeling of Phase Behavior: Determination of Cloud Point Curves Using System Temperature, Alcohol, Component Loadings as Variables It is hypothesized that carbon dioxide will act as a co-solvent for the non-polar components of the system (i.e., TAG, FAME) but will act as an anti-solvent for the polar components (i.e., DG, MG, glycerol). A balance of solvents is identified to determine where lipids are dissolved as a function of fatty acid chain length and degree of unsaturation. This balance of solvents enables tuning of system conditions to preferentially convert certain raw material over others to methyl esters and fatty acids, and therefore selectively recover methyl esters and fatty acids with desired characteristics.

Figure 12:
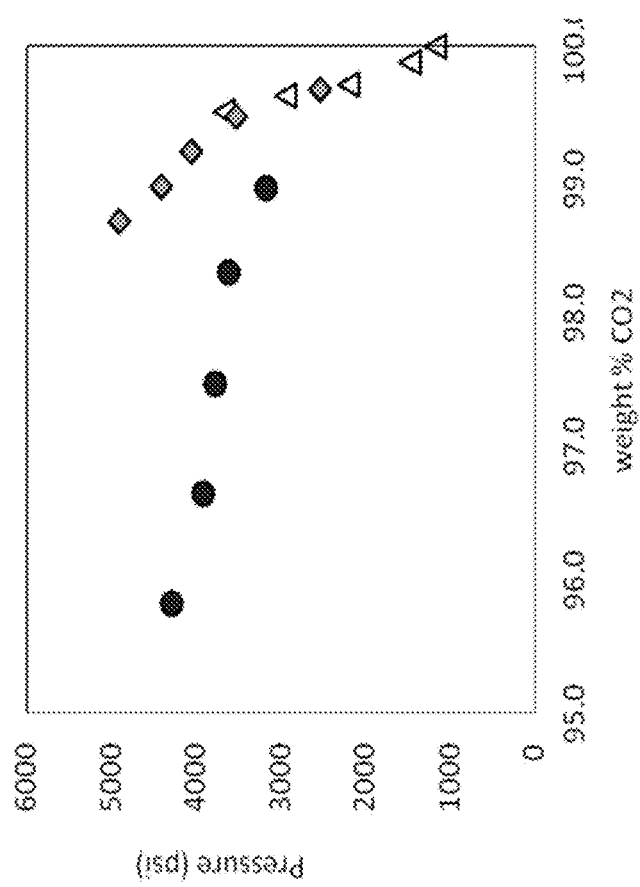
FIG. 12 is a graph illustrating preliminary cloud point curve showing the effect of methanol on the triolein cloud point in $CO_2$. Figure legend: ▲ no MeOH; ◆ 9:1 MeOH:S; ○ 90:1 MeOH:S. S=substrate (triolein, diolein, monoolein, glycerol).

Cloud point curves are experimentally constructed using a Robinson cell (Potluri et al., 2003, Fluid Phase Equilib. 211:211-217). The phase behavior of the reaction species (TAG, DG, MG, FAME, glycerol) is tested for C12, C14, C16, and C18 fatty acid series comprised varying degrees of unsaturation. The C12-C18 range is chosen due to prevalence in plant and algae biomass (Zoebelein, 2001, Dictionary of Renewable Resources. 2nd ed.; Wiley-VCH: Weinheim, Germany; Griffiths et al., 2011, J. Appl. Phycol. 24:989-1001). Cloud point curves are obtained at two different temperatures (40° C. and 60° C.) to test the effect of temperature and hence provide needed data to fit the model equations and derive the various adjustable parameters. These temperatures both are above the critical point of $CO_2$. Results showing the phase behavior of oleic acid (C18:1) are shown in FIG. 12. Glycerol was observed to be poorly soluble due to its high polarity. Triolein and monoolein produced similar cloud point curves. Although not wishing to be bound by any particular theory, these similarities may be due to the low polarity yet high molecular weight of triolein and the high polarity yet low molecular weight of monoolein. Diolein represented a balance of molecular weight and polarity, resulting in the lowest cloud point curve. Although not wishing to be bound by any particular theory, these results suggest that the optimal thermodynamic system conditions for enhanced FAME yield are those conditions where FAME are highly soluble, the starting materials and intermediates are mildly soluble, and glycerol is nearly insoluble. These conditions provide a continuous driving force on the system such that the products of transesterification (FAME and glycerol) are possibly partitioning out of the phase in which the transesterification reaction is taking place.

The transesterification reaction rate is evaluated and improved by varying the amount of methanol used in the system. Both high and low stoichiometric loadings (90:1 and 9:1 alcohol:substrate molar ratio) are tested. The smaller ratio of 9:1 represents a 3× molar excess of methanol as compared to substrate to move from second order to pseudo first order kinetics, where the reaction rate would be independent of the methanol loading. As the transesterification reaction proceeds, the decrease in available methanol is faster than the decrease of available triacylglyceride due to the necessary 3:1 methanol:triacylglyceride stoichiometric ratio of the reaction. Therefore, the actual amount of methanol would be changing throughout the reaction and would be significantly reduced at the end of the reaction when compared to the initial amount of methanol added to the reaction. This variation in the amount of methanol available for the transesterification reaction leads to significant changes in phase behavior during the course of the reaction. Therefore it is hypothesized that a higher ratio of methanol to substrate (90:1 versus 9:1, which is an increase by an order of magnitude) is more likely to show stable phase behavior during the reaction. Results of the effect of methanol on the cloud point of triolein are shown in FIG. 12. The solubility of triolein in a $CO_2$:MeOH mixture was increased when compared with the solubility of triolein in $CO_2$ alone. This result is likely due to the increased polarity of the mixed solvent as compared to the polarity of $CO_2$ alone.

Perform Cloud Point Experiments on Different Substrate Sets Varying Substrate Chain Length and Degree of Unsaturation As the lipid profile of different biomass sources, particularly among microalgae, can vary greatly, the solubility of triacylglycerides with different chain lengths will vary due to the change in polarity and symmetry of the molecules. For example, longer chain lengths and fewer degrees of unsaturation in the alkyl chains leads to lower polarity. Reduced polarity of a particular triacylglyceride may cause it to be less soluble at lower pressures or in a more polar solvent. In order to examine how variations in chain length and degrees of unsaturation affect solubility of triacylglycerides, cloud point solubilities are determined for a range of different triacylglycerides and the characteristics of the fatty acid chains are correlated with solubility. These results provide information which may be useful for the determination of the optimal reaction conditions for effectively transesterifying the total triacylglyceride mixture or a selective subset of triacylglycerides therein.

To test the effect of chain length of the fatty acid on solubility, saturated alkyl chains with 12, 14, 16, and 18 carbons (C12:0, C14:0, C16:0, and C18:0, respectively) are tested. This selection of triacylglycerides are common in plant and algae biomass (Zoebelein, 2001, Dictionary of Renewable Resources. 2nd ed.; Wiley-VCH: Weinheim, Germany; Griffiths et al., 2011, J. Appl. Phycol. 24:989-1001). All versions of substrates (TAG, DG, MG, FAME) of each particular alkyl chain length is tested at 60° C. with both high and low methanol:substrate loadings (90:1 and 9:1, respectively). In order to test the effect of the degree of unsaturation of the fatty acid on solubility, C18:0, C18:1, C18:2 and C18:3 species are evaluated. It is hypothesized that as the polarity of the fatty acid increases (by decreasing FA chain length and/or increasing the degree of unsaturation of the chain), the solubility of the substrate will increase, resulting in lower critical pressures on the cloud point curve. These results provide information which may be useful for the determination of reaction conditions which confer sufficient solubility for each species of TAG in a CO2:methanol mixture.

Phase Behavior Model of the Ternary System ($CO_2$/MeOH/Substrate)

The SAFT model is used to describe the phase behavior of the reaction system during the esterification of TAGs in a methanol/$CO_2$ mixture. The key variables in the model description are the initial methanol:$CO_2$ ratio, pressure, and temperature of the system. As the reaction proceeds, methanol is consumed and products are generated, resulting in a possible change in the phase behavior. In some instances, the pressure of the system may be adjusted to maintain the desired phase behavior.

Pure component data for methanol and $CO_2$ are readily available. In some cases, SAFT pure component and binary parameters are known, while unknown binary interaction parameters are derived through fitting the SAFT model to experimental phase behavior results. Both pure component and binary parameters are fit simultaneously to the SAFT model. Finally, previously described empirical correlations (Huang and Radosz, 1991, Eng. Chem. Res. 30:1994-2005) are used for determining the pure component parameters within a series of analogous compounds, allowing prediction of parameters of the various TAGs as the FA chain length is varied. The necessary interaction parameters for the $CO_2$:methanol binary are derived from literature VLE data (Reighard et al., 1996, Fluid Phase Equilib. 123:215-230). Experimentally-measured phase behavior is used to determine the methanol-TAG and $CO_2$-TAG parameters. Both solid-liquid (melting point depression) and liquid-liquid equilibrium data are employed to determine interaction parameters.

As the reaction proceeds, both diglycerides (DG) and monoglycerides (MG) are produced in addition to the FAME product. Because it is desirable that these intermediates remain in solution in order for the reaction to proceed, the impact of DG, MG, and FAME on the phase behavior of the initial MeOH—$CO_2$-TAG ternary system is determined DG and MG are more polar than the TAG starting material, and therefore are potentially less soluble in $CO_2$. However, both DG and MG can form hydrogen bonds with methanol, thus improving their solubility in methanol, while the FAME products are less polar and therefore more soluble in $CO_2$ due to their ester functionality and a lower molecular weight when compared to DG and MG. There is a potential for solute-solute interactions among the various TAG-derived compounds, and also the possibility that the presence of the FAME could enlarge (or perhaps shrink) the single-phase region for the DGs and MGs. Solute-solute interactions can be examined experimentally (via comparison of binary, ternary, and quaternary phase behavior) and their effects incorporated into the SAFT model for the overall system using previously described methods (Park et al., 1987, Int. J. Thermophys. 8:449-471).

Glycerol is the most polar of the transesterification reaction products, and it is hypothesized that it may form a separate phase at low methanol concentrations. If the mixture conditions are set appropriately, a liquid-liquid phase envelope appears at high $CO_2$:methanol ratios in a $CO_2$:methanol:glycerol ternary system. In this ternary system, it is hypothesized that all of the system components will partition to some extent between the two phases as long as none of the system components will selectively partition into the Nafion®. This partitioning is described mathematically via SAFT. The various interaction parameters with glycerol are derived from data on its phase behavior with the system components of interest, while the glycerol self-interaction parameters are derived from pure component pVT data (Oliviera et al., 2009, Fluid Phase Equilib. 280:22-29).

Cloud Point Curves in Simplified Quaternary System

The solubility of water in sc$CO_2$ is very minimal, while the critical point of water is very high. This insolubility may prove to be advantageous for the transesterification reaction as contact between water and substrate would favor hydrolysis of TAG to produce fatty acids instead of the transesterification of TAG to produce FAME. In order to understand the solubility of each of the components in a quaternary system where not all system components are soluble, cloud point curves are repeated using methodology described elsewhere herein, and include an aqueous phase to form a quaternary system. A subset of conditions to test is chosen from the results of the cloud point curves and phase behavior model described elsewhere herein. The tests are performed using the oleate (C18:1) family and may be extended to the other alkyl chain lengths and degrees of unsaturation. The higher methanol:substrate loading (90:1) is used as the initial reaction condition. Water loadings are tested at 0.1×, 1×, and 10× the substrate loading to evaluate the impact of the water content on the phase behavior of the system and to further understand the impact of the water content on solubility and reactivity.

Phase Behavior Model for the Quaternary System

While pure $CO_2$ solubilizes very little water at high pressure (approx. 0.25%), water and methanol are completely miscible at modest pressures. It is hypothesized that the presence of methanol in the system will greatly enhance the equilibrium solubility of water, which may reduce the extent to which the methanol:$CO_2$ mixture will solubilize TAG. The phase behavior of the water-methanol-$CO_2$ ternary system and the water-methanol-$CO_2$-TAG quaternary system is evaluated in order to examine the amount of water which is extracted into the methanol-$CO_2$-TAG mixture.

Selective Transesterification Using a Heterogenous Catalyst

Figure 14:
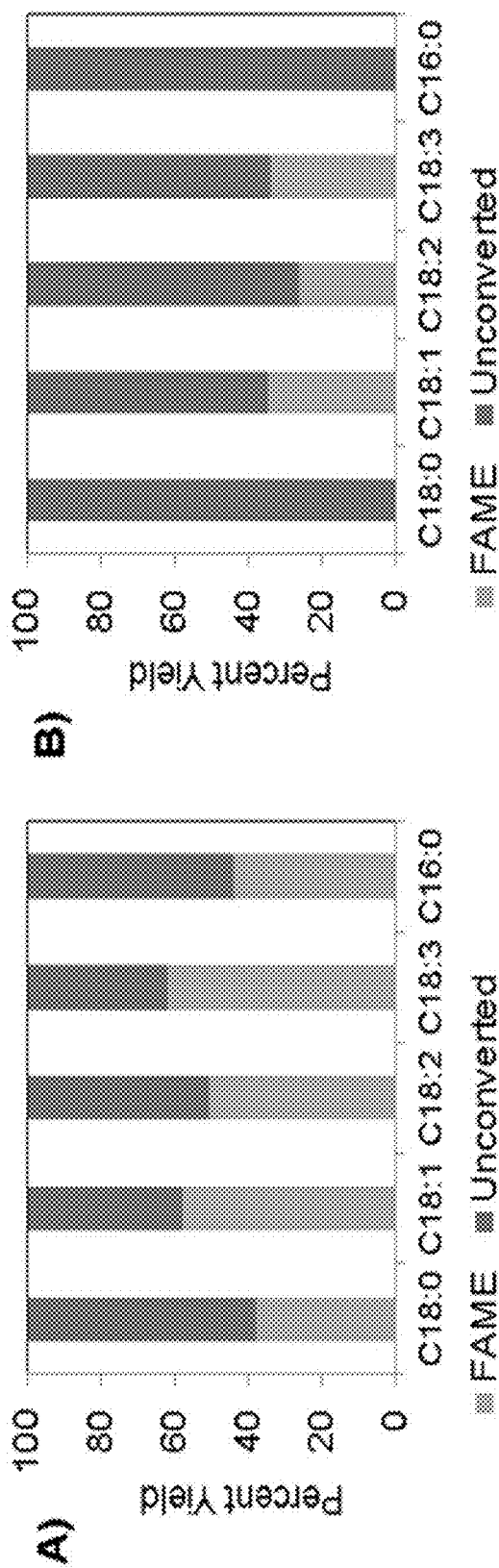
FIG. 14, comprising
Figure 18:
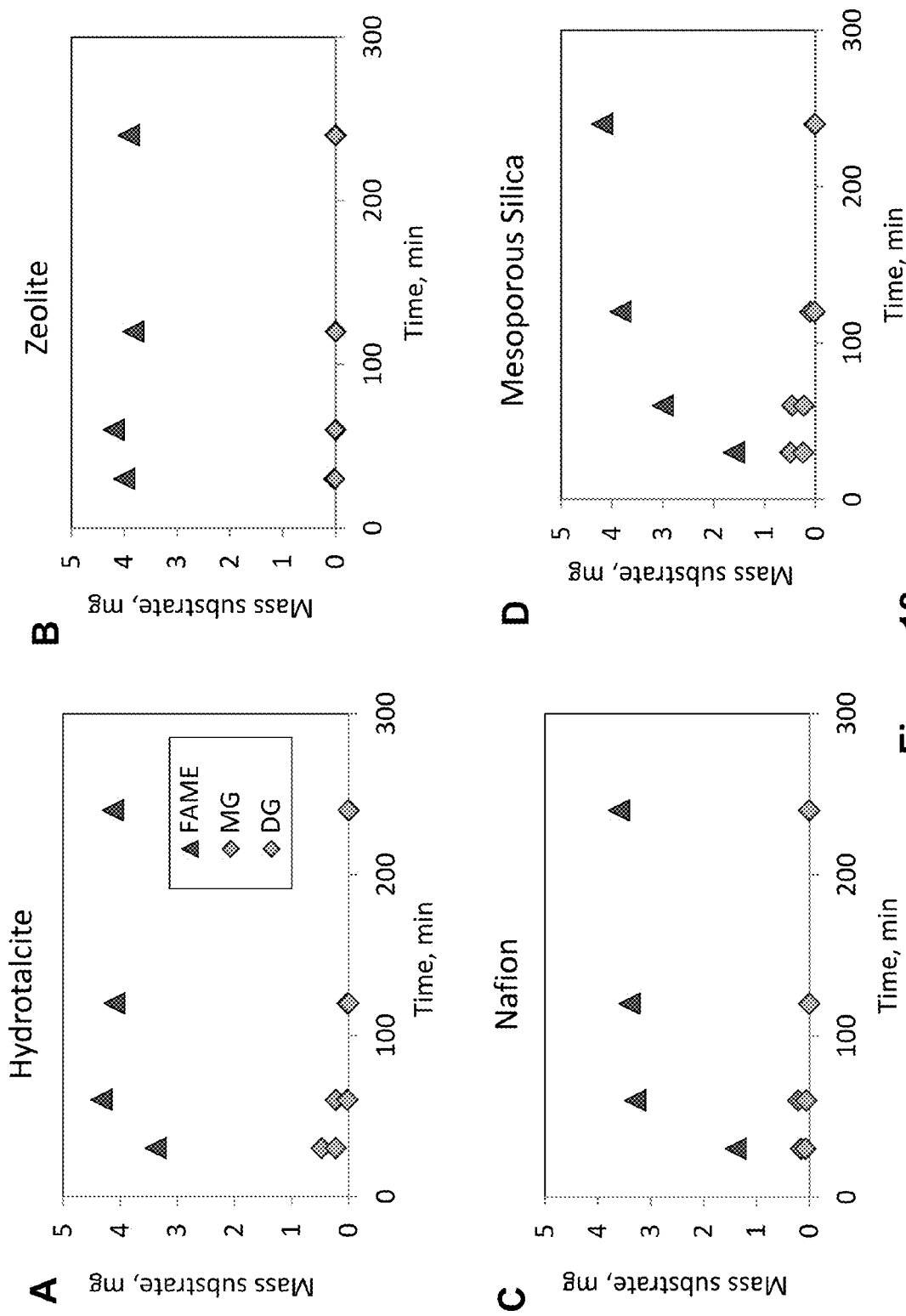
FIG. 18 illustrates the effect of different catalysts on transesterification of a triglyceride.

The effects of catalyst loading, pressure, and temperature within the system can be controlled to selectively isolate lipids from dry biomass based on polarity, chain length, or degree of unsaturation. The post-extracted biomass can be exposed to novel temperature and pressure conditions to retrieve additional lipid fraction components of interest (i.e., carotenoids, sterols). A variety of basic, neutral, and acidic heterogeneous catalysts (hydrotalcites, zeolites, mesoporous silica, Nafion®) were first screened for their potential to esterify a triglyceride at ambient pressure in methanol at 100° C. (FIG. 18). The catalysts were then screened for their ability to catalyze the transesterification of triolein to FAME under supercritical conditions and it was found that a mixed $CO_2$-methanol system, with Nafion® NR50 as a heterogeneous catalyst, produced high yields (>90%) of methyl oleate on a shorter time scale and under milder conditions than previously reported conditions. FIG. 14 shows preferred reaction conditions of >90° C. and 9.5 MPa using 3.6% methanol (v/v$_{reactor}$, ambient) and 92 mmol Nafion® NR50 catalyst per g of substrate. Although not wishing to be bound by any particular theory, energy calculations suggest that performing the transesterification reaction at this temperature may decrease the required energy inputs by nearly 70% compared to uncatalyzed reactions performed in neat supercritical methanol.

To determine if these improved product yields resulted from the role of $CO_2$ within the system, such as increased reaction rates due to increased pressure or a co-solvent effect, two control systems were explored. First, a $CO_2$-free experiment was conducted using identical reaction conditions (identical methanol, substrate, and catalyst loadings) except for the replacement of $CO_2$ with nitrogen to impart pressure. This nitrogen-containing system provided FAME yields of <5%. A second control was used to examine whether $CO_2$ was merely acting as a co-solvent within the system. In this experiment, ethyl acetate was added to the nitrogen-methanol system. While the yield of FAME increased to over 50%, it still did not attain the >95% yields observed when $CO_2$ was a component of the system. Therefore, a co-solvent, which increases solubility of the substrate in the reaction, was determined to be a necessary component of the transesterification reaction. However, these results do not fully explain the superior results observed for the $CO_2$-MeOH system at 80° C., 9.5 MPa, and 3.6% methanol (v/v$_{reactor}$, ambient) loading. Although both ethyl acetate and carbon dioxide facilitate the interaction between methanol and triolein interaction within the system, the FAME yield when using a $CO_2$-methanol co-solvent system is far greater than the FAME yield using an ethyl acetate-nitrogen-methanol system. The use of $CO_2$ confers unique properties and contribution to the solvent system.

Figure 13:
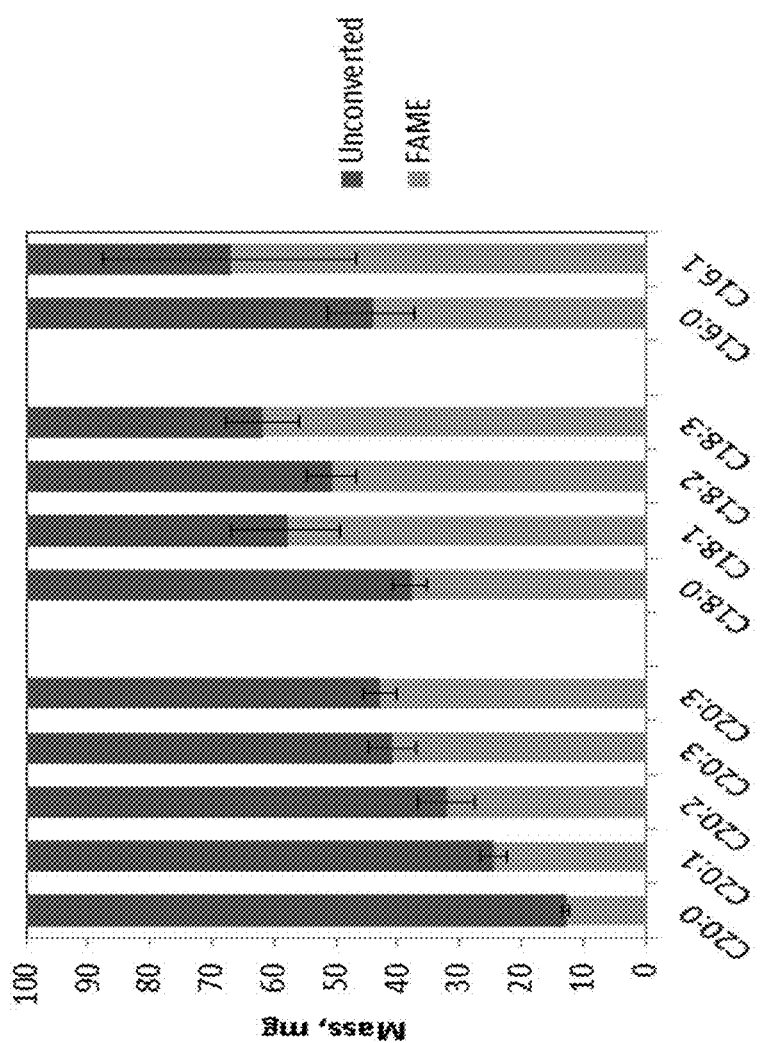
FIG. 13 is a graph illustrating model triacylglycerides that are preferentially converted to methyl esters as a function of chain length and degree of unsaturation. Reaction conditions: 95° C., 9.65 MPa, 1 h reaction, 200 mg Nafion® NR50, 5 mL methanol, 100 mg triacylglyceride (50 mL reaction volume).

It was also demonstrated that the $CO_2$-methanol system with Nafion® NR50 as the heterogenous catalyst selectively transesterifies fatty acids as a function of both chain length and degree of unsaturation (FIG. 13). Shorter chain lengths and higher degrees of unsaturation are preferentially recovered as methyl esters, making it possible to separate the fatty acid fractions which contain fatty acids that may be more suited to higher-value applications than biodiesel. Although differential solubility in pure $CO_2$ according to chain length is well known (Bharath et al., 1989, Fluid Phase Equilib. 50:315-327; Inomata et al., 1989, Fluid Phase Equilib. 46:41-52), separations based on degree of unsaturation are rare, especially in the presence of cosolvent, as a cosolvent is often reported to worsen selectivity or be ineffective at best (Nilsson et al., 1992, J. Am. Oil Chem. Soc. 69:305-308). These improvements due to selective transesterification of certain fatty acids may be useful in providing separations of fatty acids under mild conditions. Although not wishing to be bound by any particular theory, it is likely that the catalyst phase is at least partly responsible for the observed selectivity toward unsaturated fatty acid species, either through differential partitioning into the catalyst phase or differential reactivity of the individual species.

The reactivity of triacylglycerides, diglycerides, and monoglycerides in the sc$CO_2$ and methanol system, and the effects of mass transfer limitations (i.e., mixing speed; catalyst particle size) are examined Reactions are tested in a specifically machined reactor (Lepilleur and Beckman, 1997, Macromolecules 30:745-756) made of a single piece of stainless steel with an internal volume of ca. 55 mL and containing two sapphire view windows. The reactor body has several ports for sampling and heating elements controlled by a thermocouple and temperature controller. The effects of a number of variables on the transesterification reaction are explored, such as the use of substrates (triacylglyceride, diglyceride, or monoglyceride) within the system and/or varying FA chain lengths from C12:0 to C18:0 and FA chain unsaturation from C18:0 to C18:3.

The loading of different components including methanol, $CO_2$, and lipid, is also examined. In one embodiment, the component loadings of the system include a methanol loading of 3.6% and 10% (v/v$_{reactor}$, ambient), a substrate loading of 100 mg or 1 g, and the addition of $CO_2$ achieve a pressure of 9.65 MPa at 95° C.

The properties of the catalyst, including the effect of pre-treating the catalyst, are also studied. Different formulations of the catalyst are compared within the system, such as Nafion® NR50 powder (0.4 mm diameter) versus Nafion® NR50 beads (7-9 mm) Both of these catalysts have equivalent density of ion exchange capacity (0.9 meq/g). It is hypothesized that the smaller particle size of the Nafion® NR50 powder will contribute to enhanced reaction rates by reducing internal mass transfer. The Nafion® NR50 series is also compared to the Nafion® SAC13 series, which is on a solid support. Regarding catalyst pre-treatment, Nafion® particles are pre-soaked in methanol, with characterization of the porosity determined by previously described methods (e.g. BET) (Lopez and Good win Jr., 2007, J. Catal. 245: 381-391; Galia et al., 2011, J. Supercrit. Fluid 56:186-193). It is hypothesized that soaking the Nafion® in methanol will result in swelled pores and decreased mass transfer limitations, thereby permitting faster reaction rates.

Representative primary, secondary, and tertiary phase ($CO_2$-methanol-lipid) conditions are examined to highlight how these variables will affect the system. A reaction time of 1 hour is used for both stirred and unstirred conditions at 60° C. and 80° C. The results of this screening provide a more specific timeframe for reaction and sampling protocols to better understand the reaction kinetics. These results may also be useful in supplying system conditions for the treatment of crude biomass within the system.

Use of Dry Biomass within a Test System

The presence of actual biomass in the system may change the reaction behavior. Under identical conditions, transesterification of each of a pure triacylglyceride (tripalmitin, tristearin, triolein, trilinolein, and trilinolenin) yields significant amounts of corresponding methyl esters (FIG. 14A), but treatment of a mixture comprised of 20% of each triacylglyceride leads to preferential conversion of the unsaturated species (FIG. 14B) and a reduction in overall yields.

Lyophilized algae biomass is used as the initial starting material to eliminate water as a confounding variable within the reaction. *Isochrysis galbani* (clone T-ISO) is provided by AgriFuels (East Hartford, Conn.). This strain is selected for its variety of potential applications including biodiesel and animal nutrition, as well as its ease of growth, density of growth, and high lipid content. The preferred conditions (i.e., component loadings, catalyst properties, pre-treatment, and location) are tested on varying amounts of biomass under reaction conditions determined elsewhere herein for selective transesterification using a heterogenous catalyst.

Comparison of a Single Reactor to Serial Processing

To the best of knowledge, this is the first example of an in situ, supercritical biomass extraction and fractionation process to produce a tunable array of products. The extraction and conversion conditions are controlled to demonstrate preferential recovery of shorter-chain, unsaturated fatty esters followed by longer-chain, saturated fatty esters and finally polar lipids such as β-carotene. By characterizing all extracted fractions as well as residual biomass, a techno-economic analysis based on available market data can be carried out to provide system conditions that divert biomass components to the most economic applications.

Techno-Economic Analysis models are used to identify the major factors that can cause technical or economic infeasibility. These can be related to technology inputs, output reliability, capital costs, and operational energy costs. NREL has established TEA models for crop- and microalgal biofuels produced (Bush et al., 2008, NREL/CP-150-43153: Using System Dynamics to Model the Transition to Biofuels in the United States. Proceedings of the Third International Conference on Systems of Systems Engineering, Monterey, Calif.). This TEA model is revised to adjust inputs/outputs from the bench-scale findings for extraction, fractionation, and transformation. All models describe a fully integrated facility designed for production of biofuels and bio-based chemicals. The TEA models are used to determine the linkages between production costs and input costs (energy, water, and nutrients) to determine how these biobased products will compare with comparable products produced from petrochemicals undergoing perturbations and disruptions caused by raw material scarcities and environmental changes. TEA helps identify scenarios in which biobased products can compete with the products they are meant to replace, and also confirms if the system proposed here is a critical path element in which technical progress leads to economically viable solutions.

Characterization of a One-Pot Extraction/Conversion/Fractionation Process Using Model Lipids A one-pot extraction/conversion/fractionation process is examined in order to determine whether water interferes with the overall process (FIG. 16). Water may interfere with the process via hydrolysis of TAGs to free fatty acids, or by reduced solubility of TAGs and intermediate species in a $CO_2$-rich methanol phase. If the solubility of Tags and intermediate species is reduced, a balance between added energy input to dewater biomass or crude lipids in advance of methanol-$CO_2$ exposure, and added energy input required if higher pressures and temperatures are needed to solubilize TAG may be required. The results of the model system which includes partitioning of water (likely between glycerol and $CO_2$-methanol phases) and the determined preferred conditions for the production of FAME assist in the determination for the initial system conditions for the transesterification of model lipids in the presence of water. The transesterification of the C18:0 to C18:3 (tristearin to trilinolenin) triacylglyceride series is evaluated in order to acertain the effects of water on the overall yield of the reaction in addition to the selectivity of the transesterification reaction when compared to the "dry" biomass system.

Characterization of a One-Pot Extraction/Conversion/Fractionation using Crude, Undried Biomass The one-pot extraction/conversion/fractionation system is evaluated with a concentrated algae slurry, where the algae is harvested via centrifugation. *Isochrysis galbani* (clone T-ISO), which is described elsewhere herein and is provided by AgriFuels (East Hartford, Conn.) is used for the biomass. Based on previous experiments, centrifugation was found to provide about 4% solids content in the wet algae slurry with potential for further dewatering if necessary. The centrifuged slurry is compared to reconstituted freeze-dried samples of the same algae to determine if the levels of cell disruption make the process more or less efficient based on mass transfer of the solvent mixture into the cell.

Samples of waste restaurant oil are obtained from Greenleaf Biofuels (New Haven, Conn.). Used oil typically contains significant amounts of water as well as numerous contaminants from food and thermally- or oxidatively-degraded products of the naturally occurring lipids. The water content and lipid profile are characterized according to known methods.

Comparison of a Single Reactor to Serial Processing

The extraction of lipids in supercritical fluids is tolerant of water. Therefore, a serial processing system may be useful for the recovery of lipids from wet biomass and subsequent separation into pure fractions without sacrificing yield and selectivity upon transesterification.

A one-pot extraction and transesterification (FIG. 15) procedure is compared to serial processing using a separate reactor for each process (FIG. 16). An extractor-convertor system (FIG. 16) is used for the processing of *I. galbani* biomass in addition to waste restaurant oil. Technoeconomic analysis is performed to improve the portfolio of potential products originating from wet crude biomass processed through the system.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for producing a fatty acid methyl ester (FAME) from a lipid source, the method comprising:
   (a) extracting at least one lipid from a lipid source; and
   (b) transesterifying the at least one lipid into a FAME, wherein steps (a) and (b) occur within a system comprised of a first solvent and a second solvent, and at least one catalyst.

2. The method of claim 1, further comprising a step of fractionating the FAME from the system.

3. The method of claim 1, wherein the at least one lipid is a triacylglyceride (TAG).

4. The method of claim 1, wherein the lipid source comprises biomass.

5. The method of claim 4, wherein the biomass comprises algae.

6. The method of claim 4, wherein the biomass is dry biomass.

7. The method of claim 4, wherein the biomass is wet biomass.

8. The method of claim 1, wherein the first solvent is a polar solvent.

9. The method of claim 8, wherein the polar solvent is methanol.

10. The method of claim 1, wherein the first solvent is present within the system at a volume of about 3.6% v/v.

11. The method of claim 1, wherein the second solvent is a supercritical fluid.

12. The method of claim 11, wherein the supercritical fluid is supercritical carbon dioxide.

13. The method of claim 1, wherein the catalyst is a heterogenous catalyst.

14. The method of claim 13, wherein the heterogenous catalyst is Nafion®.

15. The method of claim 1, wherein the system is heated to a temperature no greater than about 95° C.

16. The method of claim 1, wherein the system is heated to a temperature no greater than about 80° C.

17. The method of claim 1, wherein the system is pressurized to a pressure of about 9.5 MPa.

18. The method of claim 1, wherein the system is pressurized to a pressure of about 9.65 MPa.

19. The method of claim 1, wherein the system is pressurized to a pressure of about 17.5 MPa.

20. The method of claim 1, wherein the system has a reaction time of at least 2 hours.

21. A method for selectively producing a fatty acid methyl ester (FAME) from a lipid source, the method comprising:
    (a) extracting at least one lipid from a lipid source;
    (b) selectively transesterifying the at least one lipid into a FAME, and
    (c) fractionating the FAME, wherein the lipid source is comprised of a mixture of lipids, further wherein steps (a) and (b) occur within a system, further wherein the system is comprised of a first solvent and a second solvent, and further wherein the system is comprised of a catalyst.

22. The method of claim 21, wherein the at least one lipid is a triacylglyceride (TAG).

23. The method of claim 21, wherein the lipid source comprises biomass.

24. The method of claim 23, wherein the biomass comprises algae.

25. The method of claim 23, wherein the biomass is dry biomass.

26. The method of claim 23, wherein the biomass is wet biomass.

27. The method of claim 21, wherein the first solvent is a polar solvent.

28. The method of claim 27, wherein the polar solvent is methanol.

29. The method of claim 21, wherein the first solvent is present within the system at a volume of about 3.6% v/v.

30. The method of claim 21, wherein the second solvent is a supercritical fluid.

31. The method of claim 30, wherein the supercritical fluid is supercritical carbon dioxide.

32. The method of claim 21, wherein the catalyst is a heterogenous catalyst.

33. The method of claim 32, wherein the heterogenous catalyst is Nafion®.

34. The method of claim 21, wherein the system is heated to a temperature no greater than about 95° C.

35. The method of claim 21, wherein the system is heated to a temperature no greater than about 80° C.

36. The method of claim 21, wherein the system is pressurized to a pressure of about 9.5 MPa.

37. The method of claim 21, wherein the system is pressurized to a pressure of about 9.65 MPa.

38. The method of claim 21, wherein the system is pressurized to a pressure of about 17.5 MPa.

39. The method of claim 21, wherein the system has a reaction time of at least 2 hours.

* * * * *